United States Patent [19]
Yoon

[11] Patent Number: 5,993,467
[45] Date of Patent: *Nov. 30, 1999

[54] SUTURING INSTRUMENT WITH ROTATABLY MOUNTED SPREADABLE NEEDLE HOLDER

[76] Inventor: InBae Yoon, 2101 Highland Ridge Dr., Phoenix, Md. 21131

[*] Notice: This patent issued on a continued prosecution application filed under 37 CFR 1.53(d), and is subject to the twenty year patent term provisions of 35 U.S.C. 154(a)(2).

[21] Appl. No.: 08/904,764

[22] Filed: Aug. 1, 1997

Related U.S. Application Data

[63] Continuation-in-part of application No. 08/758,648, Nov. 27, 1996, Pat. No. 5,759,188, application No. 08/847,182, May 1, 1997, and application No. 08/877,764, Jun. 17, 1997.

[51] Int. Cl.⁶ .................................................... A61B 17/04
[52] U.S. Cl. ............................................ 606/147; 606/148
[58] Field of Search .............................. 606/139, 144–148

[56] References Cited

U.S. PATENT DOCUMENTS

| | | |
|---|---|---|
| 919,138 | 4/1909 | Drake et al. . |
| 1,037,864 | 9/1912 | Carlson et al. .......................... 606/147 |
| 1,131,163 | 3/1915 | Saunders et al. . |
| 1,155,378 | 10/1915 | Steedman . |
| 1,449,087 | 3/1923 | Bugbee .................................... 606/144 |
| 1,822,330 | 9/1931 | Ainslie .................................... 606/148 |
| 1,916,722 | 7/1933 | Ende . |
| 2,213,830 | 9/1940 | Anastasi . |
| 2,580,964 | 1/1952 | Skaller . |
| 2,601,564 | 6/1952 | Smith . |
| 2,646,045 | 7/1953 | Priestley . |
| 2,959,172 | 11/1960 | Held . |
| 3,090,386 | 5/1963 | Curtis . |
| 3,139,089 | 6/1964 | Schwerin . |
| 3,349,772 | 10/1967 | Rygg ....................................... 606/147 |
| 3,470,875 | 10/1969 | Johnson ................................. 606/147 |
| 3,842,840 | 10/1974 | Schweizer .............................. 606/148 |
| 3,946,740 | 3/1976 | Bassett .................................... 606/148 |
| 4,109,658 | 8/1978 | Hughes . |
| 4,164,225 | 8/1979 | Johnson et al. ........................ 606/147 |
| 4,257,420 | 3/1981 | Terayama . |

(List continued on next page.)

FOREIGN PATENT DOCUMENTS

| | | |
|---|---|---|
| 482881A1 | 4/1992 | European Pat. Off. . |
| 0337579 | 4/1904 | France . |
| 0395073 | 8/1973 | U.S.S.R. . |
| 2260704A | 9/1991 | United Kingdom . |
| WO 97/37583 | 10/1997 | WIPO . |

*Primary Examiner*—Gary Jackson
*Attorney, Agent, or Firm*—Blank Rome Comisky & McCauley LLP

[57] ABSTRACT

An instrument for suturing anatomical tissue with a suture needle includes a housing, an elongate shaft having a proximal end mounted by the housing and a distal end with a peripheral edge, and a needle holder protruding from the distal end of the elongate shaft and having a needle holding member at a distal end operable to grasp and release a suture needle. A distal portion of the needle holder extends laterally outward at an angle from a first longitudinal axis of the elongate shaft to a position where at least a portion of the corresponding needle holding members are spaced laterally outward of the peripheral edge of the elongate shaft. In addition, the needle holder is rotatable about the first longitudinal axis of the elongate shaft to cause the corresponding needle holding members to move along an arcuate path. When inserting the suturing instrument through a portal in an endoscopic procedure, the needle holder is preferably movable to an undeployed position where their needle holding members are spaced laterally inward of the peripheral edge of the elongate shaft. When suturing, the needle holding members can be moved from their undeployed position to a deployed position disposed laterally outward of the peripheral edge due to the angled configuration of the distal portion of the needle holder.

28 Claims, 8 Drawing Sheets

U.S. PATENT DOCUMENTS

| | | | |
|---|---|---|---|
| 4,440,171 | 4/1984 | Nomoto et al. | 606/147 |
| 4,557,265 | 12/1985 | Andersson . | |
| 4,621,640 | 11/1986 | Mulhollan et al. | 606/147 |
| 4,635,638 | 1/1987 | Weintraub et al. . | |
| 4,935,027 | 6/1990 | Yoon . | |
| 5,037,433 | 8/1991 | Wilk et al. . | |
| 5,100,421 | 3/1992 | Christoudias . | |
| 5,147,373 | 9/1992 | Ferzli . | |
| 5,152,769 | 10/1992 | Baber . | |
| 5,171,257 | 12/1992 | Ferzli . | |
| 5,181,919 | 1/1993 | Bergman et al. . | |
| 5,209,741 | 5/1993 | Spaeth | 604/280 |
| 5,211,650 | 5/1993 | Noda | 606/139 |
| 5,222,508 | 6/1993 | Contarini | 606/139 |
| 5,224,948 | 7/1993 | Abe et al. . | |
| 5,234,443 | 8/1993 | Phan et al. . | |
| 5,244,948 | 9/1993 | Mulhaupt et al. . | |
| 5,261,917 | 11/1993 | Hasson et al. . | |
| 5,281,238 | 1/1994 | Chin et al. . | |
| 5,300,082 | 4/1994 | Sharpe et al. . | |
| 5,304,185 | 4/1994 | Taylor | 606/147 |
| 5,305,121 | 4/1994 | Moll . | |
| 5,308,353 | 5/1994 | Beurrier . | |
| 5,320,632 | 6/1994 | Heidmueller | 606/144 |
| 5,336,230 | 8/1994 | Leichtling et al. . | |
| 5,336,231 | 8/1994 | Adair . | |
| 5,356,424 | 10/1994 | Buzerak et al. . | |
| 5,364,408 | 11/1994 | Gordon . | |
| 5,364,409 | 11/1994 | Kuwabara et al. | 606/148 |
| 5,374,275 | 12/1994 | Bradley et al. . | |
| 5,376,096 | 12/1994 | Foster | 606/147 |
| 5,389,098 | 2/1995 | Tsuruta et al. . | |
| 5,389,103 | 2/1995 | Melzer et al. . | |
| 5,395,367 | 3/1995 | Wilk . | |
| 5,397,325 | 3/1995 | Della Badia et al. . | |
| 5,403,328 | 4/1995 | Shallman | 606/144 |
| 5,403,329 | 4/1995 | Hinchcliffe | 606/147 |
| 5,437,681 | 8/1995 | Meade et al. | 606/145 |
| 5,454,823 | 10/1995 | Richardson et al. . | |
| 5,462,561 | 10/1995 | Voda | 606/144 |
| 5,462,562 | 10/1995 | Elkus | 606/148 |
| 5,468,251 | 11/1995 | Buelna | 606/223 |
| 5,470,338 | 11/1995 | Whitfield et al. . | |
| 5,474,057 | 12/1995 | Makower et al. . | |
| 5,474,568 | 12/1995 | Scott | 606/144 |
| 5,477,794 | 12/1995 | Klundt . | |
| 5,478,344 | 12/1995 | Stone et al. . | |
| 5,478,345 | 12/1995 | Stone et al. . | |
| 5,480,406 | 1/1996 | Nolan et al. . | |
| 5,496,310 | 3/1996 | Exconde et al. | 606/205 |
| 5,496,334 | 3/1996 | Klundt et al. . | |
| 5,503,634 | 4/1996 | Christy . | |
| 5,520,703 | 5/1996 | Essig et al. . | |
| 5,540,704 | 7/1996 | Gordon et al. . | |
| 5,540,705 | 7/1996 | Meade et al. . | |
| 5,545,148 | 8/1996 | Wurster . | |
| 5,562,640 | 10/1996 | McCabe et al. . | |
| 5,562,685 | 10/1996 | Mollenauer et al. . | |
| 5,562,686 | 10/1996 | Sauer et al. . | |
| 5,562,703 | 10/1996 | Desai . | |
| 5,569,164 | 10/1996 | Lurz . | |
| 5,569,269 | 10/1996 | Hart et al. . | |
| 5,569,270 | 10/1996 | Weng . | |
| 5,573,542 | 11/1996 | Stevens . | |
| 5,578,048 | 11/1996 | Pasqualucci et al. . | |
| 5,582,617 | 12/1996 | Klieman et al. . | |
| 5,591,181 | 1/1997 | Stone et al. . | |
| 5,601,575 | 2/1997 | Measamer et al. | 606/147 |
| 5,603,718 | 2/1997 | Xu . | |
| 5,607,435 | 3/1997 | Sachdeva et al. | 606/139 |
| 5,609,601 | 3/1997 | Kolesa et al. . | |
| 5,626,588 | 5/1997 | Sauer et al. | 606/144 |
| 5,632,751 | 5/1997 | Piraka | 606/139 |
| 5,632,752 | 5/1997 | Buelna | 606/144 |
| 5,643,292 | 7/1997 | Hart | 606/144 |
| 5,662,663 | 9/1997 | Shallman | 606/144 |
| 5,674,230 | 10/1997 | Tovey et al. | 606/139 |
| 5,702,407 | 12/1997 | Kaji . | |
| 5,707,379 | 1/1998 | Fleenor et al. | 606/145 |
| 5,709,693 | 1/1998 | Taylor | 606/145 |
| 5,709,694 | 1/1998 | Greenberg et al. | 606/148 |
| 5,713,908 | 2/1998 | Jameel et al. | 606/148 |
| 5,722,990 | 3/1998 | Sugarbaker et al. | 606/207 |
| 5,810,805 | 9/1998 | Sutcu et al. . | |

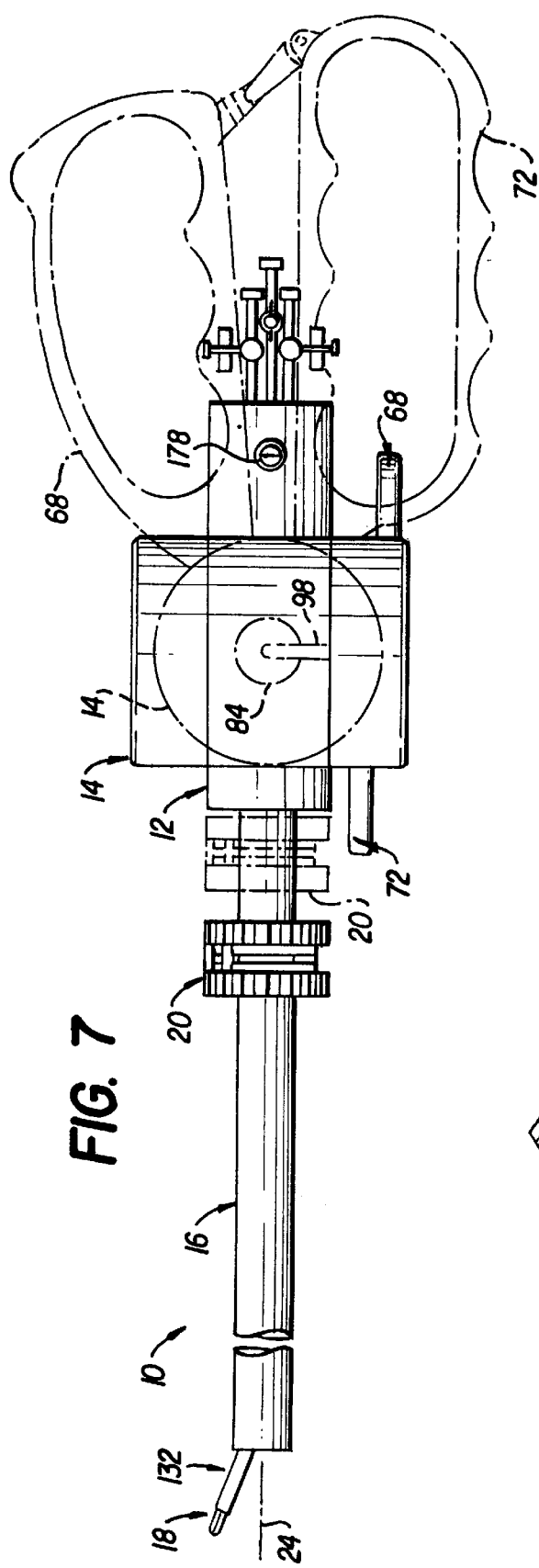
FIG. 7
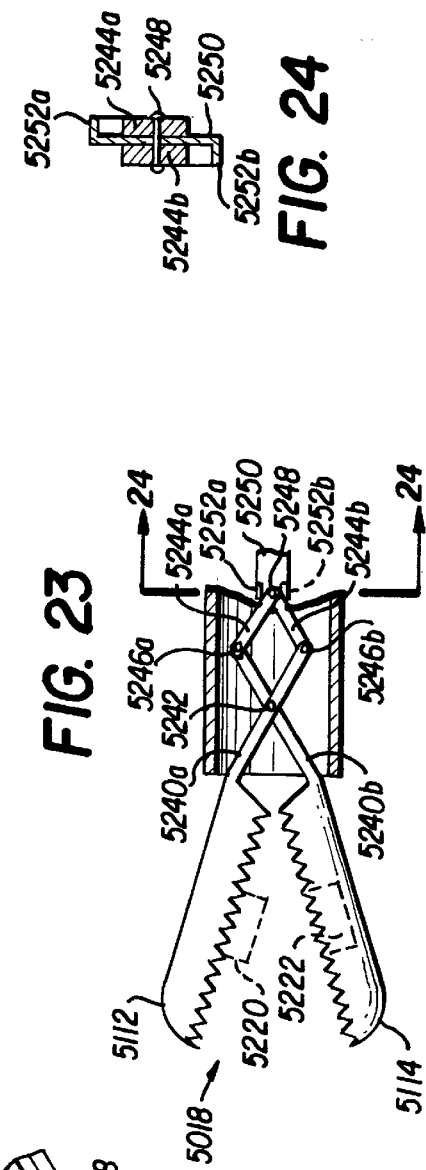
FIG. 24
FIG. 23
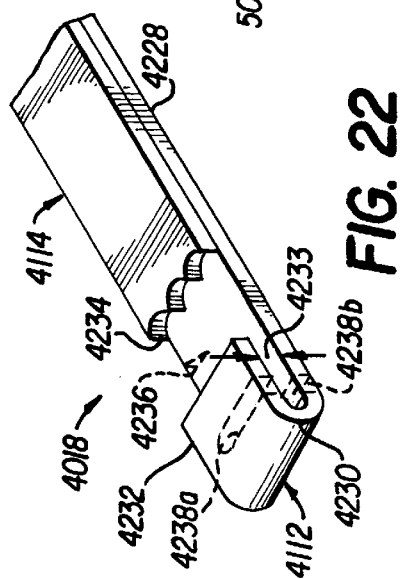
FIG. 22

SUTURING INSTRUMENT WITH ROTATABLY MOUNTED SPREADABLE NEEDLE HOLDER

CROSS-REFERENCE TO RELATED APPLICATIONS

This application is a continuation-in-part of application Ser. No. 08/758,648, filed Nov. 27, 1996, now U.S. Pat. No. 5,759,188 Ser. No. 08/847,182, filed May 1, 1997, and Ser. No. 08/877,764, filed Jun. 17, 1997, the disclosures of which are incorporated herein by reference.

BACKGROUND OF THE INVENTION

1. Field of the Invention

The present invention pertains to suturing of bodily or anatomical tissue and, more particularly, to an apparatus and method for suturing anatomical tissue during endoscopic and open surgical procedures.

2. Discussion of the Related Art

Suturing of bodily tissue, that is, the practice of using lengths of suture material to ligate or approximate tissue, is a time consuming part of most surgical procedures including both open surgery and endoscopic or closed surgery. By "open surgery" is meant surgery wherein the surgeon gains access to the surgical site by a relatively large incision and by "endoscopic surgery" is meant minimally invasive surgery wherein the surgeon gains access to the surgical site via one or more portals through which endoscopes are introduced to view the surgical site and through which instruments, such as forceps, cutters, needle holders and the like, are introduced to the surgical site.

In the past, suturing has been accomplished with the use of a sharp suture needle carrying a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and to control approximation, occlusion, attachment or other conditions of the tissue.

The process of tissue penetration and knotting of the suture material can be time consuming and tedious work, particularly when performed in connection with microsurgery and endoscopic surgery and can unduly prolong the duration of surgery and therefore the period during which the patient is under anesthesia. Nevertheless, endoscopic surgery is preferred over open surgery due to the greatly reduced trauma and wound healing time for the patient and due to cost savings associated with shorter hospital stays and performing surgery in non-hospital or out-patient surgery sites. Accordingly, there has been much effort to develop techniques for facilitating the suturing normally performed by use of a suture needle and a length of suture material. Alternative techniques proposed have included electrical coagulation, mechanical devices such as clips, clamps and staples, and lasers; however, no alternative technique has yet been well accepted by surgeons to produce the results obtained by suturing and tying. Thus, there is a great need for suturing techniques useful in endoscopic surgery to permit surgeons to suture anatomical tissue using suture needles and lengths of suture material in a time efficient, consistent and precise manner.

The performance of an endoscopic procedure typically involves creation of one or a number of puncture sites through a wall of an anatomical cavity using a penetrating instrument including an obturator, such as a trocar, disposed within a portal sleeve. After the penetrating instrument has penetrated into the anatomical cavity, the obturator is withdrawn leaving the sleeve in place to form a portal in the cavity wall for the introduction of instruments such as endoscopes, scissors, forceps, needle holders and the like into the anatomical cavity. Suturing is typically performed with a needle holding instrument or needle holder having a pair of jaws adapted to hold the body of a suture needle. The jaws of the needle holding instrument are inserted through the portal sleeve and are positioned at the operative site by manipulation of a handle at the proximal end of the instrument outside the body. With a suture needle held between the jaws of the needle holding instrument, the handle is manipulated to cause a tip of the needle to be pushed through the tissue being sutured. Once the tip of the suture needle has been pushed through the tissue, the jaws of the needle holding instrument must either be opened to release the suture needle so that the tip of the needle can be grasped and pulled through the tissue therewith, or a second needle holding instrument must be introduced at the operative site through another portal to grasp the tip of the suture needle after it has emerged from the tissue being sutured. The former technique requires further adjustment of the suture needle within the jaws of the needle holder before another stitch can be made; and, while use of a second needle holding instrument for pulling the needle through the anatomical tissue allows the first needle holding instrument to grasp the body of the suture needle in the manner required to make additional stitches, it is generally desirable to minimize the number of puncture sites created for performing a particular endoscopic procedure.

SUMMARY OF THE INVENTION

Accordingly, it is a primary object of the present invention to overcome the above-mentioned disadvantages of the prior art and to improve suturing instruments and methods of suturing anatomical tissue.

Another object of the present invention is to permit suturing of anatomical tissue without the need of having to use multiple needle holding instruments.

Yet another object of the present invention is to minimize the number of puncture sites required for suturing anatomical tissue in an endoscopic procedure by inserting a needle holder through a single portal with a suturing instrument that is operable to move the needle holder to suture anatomical tissue.

It is a further object of the present invention to permit a suturing instrument as well as other medical instruments and devices to be introduced through a single portal in an endoscopic procedure without the need of having to withdraw the suturing instrument from the portal.

An additional object of the present invention is to increase the range of relative movement or working span of a needle holder inserted through a single portal with a suturing instrument in an endoscopic procedure without the need of having to increase the size of the portal.

Some of the advantages of the present invention over the prior art are that suturing of anatomical tissue in an endoscopic procedure can be accomplished using standard suture needles and filamentous suture materials in a time efficient, consistent and precise manner, that relatively long suture needles can be used to suture thick tissue without the need of having to insert additional instruments at the operative site, that single-handed suturing is made possible, that conventional handle structures can be used to provide users with a familiar feel and to decrease adaptation time, and that the instrument can be made sterilizable for reuse or disposable for single patient use as desired.

The present invention is generally characterized in an instrument for suturing anatomical tissue with a suture needle including a housing, an elongate shaft having a proximal end mounted by the housing and a distal end with a peripheral edge, and a needle holder protruding from the distal end of the elongate shaft and having a needle holding member at a distal end operable to grasp and release a suture needle. A distal portion of the needle holder extends laterally outward at an angle from a first longitudinal axis of the elongate shaft to a position where at least a portion of the corresponding needle holding member is spaced laterally outward of the peripheral edge of the elongate shaft. In addition, the needle holder is rotatable about the first longitudinal axis of the elongate shaft to cause the corresponding needle holding member to move along a first arcuate path having a center of curvature coaxial with the first longitudinal axis. When inserting the suturing instrument through a portal in an endoscopic procedure, the needle holder is preferably movable to an undeployed position where the needle holding member is spaced laterally inward of the peripheral edge of the elongate shaft. When suturing, however, the needle holding member can be moved from the undeployed position to a deployed position disposed laterally outward of the peripheral edge due to the angled configuration of the distal portion of the needle holder. One or more operating channels are preferably defined through the elongate shaft to provide access to the operative site from outside the body.

An additional aspect of the present invention is generally characterized in a method of suturing anatomical tissue using a length of suture material attached to a suture needle, the method including the steps of grasping the suture needle with a needle holder protruding distally from the distal end of an elongate shaft, the needle holder including a distal portion extending laterally outward at an angle from a first longitudinal axis of the elongate shaft to a needle holding member disposed at least partly outside a peripheral edge of the elongate shaft, positioning a tip of the suture needle adjacent the anatomical tissue, driving the suture needle through the anatomical tissue along an arcuate path by rotating the needle holder in a first direction, releasing the suture needle from the needle holder, repositioning the needle holder to receive the tip of the suture needle by rotating the needle holder in a second direction opposite the first direction, regrasping the suture needle with the needle holder, and pulling the suture needle through the anatomical tissue by rotating the needle holder in the first direction.

Other objects and advantages of the present invention will become apparent from the following description of the preferred embodiments taken in conjunction with the accompanying drawings, wherein like parts in each of the several figures are identified by the same reference numerals or by reference numerals having the same last three digits.

BRIEF DESCRIPTION OF THE DRAWINGS

FIG. 7 is a top view, broken longitudinally, of the suturing instrument according to the present invention with the needle holder in an axially extended, deployed position.

FIG. 22 is a fragmentary perspective view of still another modification of a needle holder for use with a suturing instrument according to the present invention.

FIG. 23 is a fragmentary side view, partly in section, of yet another modification of a needle holder for use with a suturing instrument according to the present invention.

FIG. 24 is a cross-sectional view of the needle holder shown in FIG. 23 taken through line 24—24.

DETAILED DESCRIPTION OF THE PREFERRED EMBODIMENTS

Figure 1:
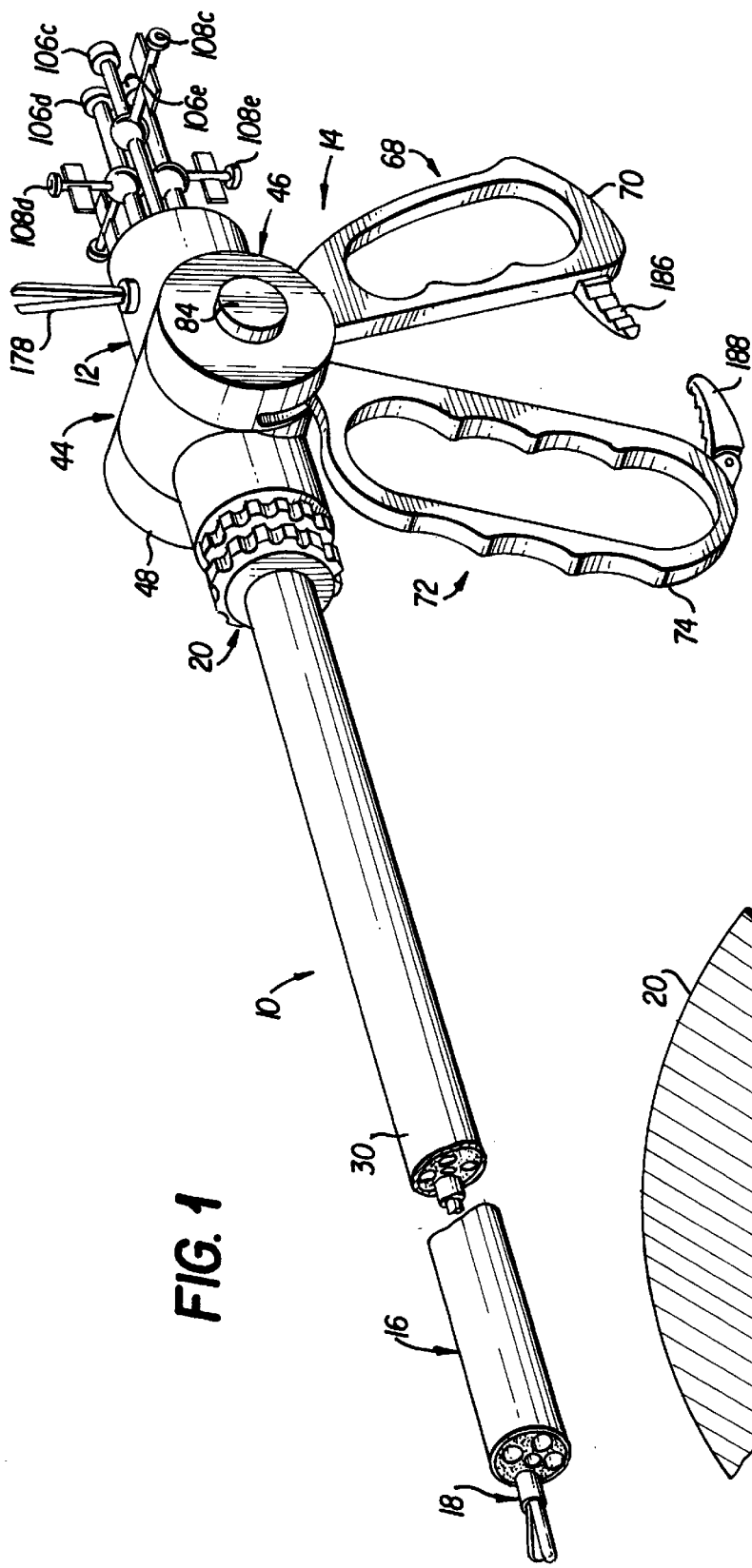
FIG. 1 is a perspective view, broken longitudinally, of a suturing instrument according to the present invention.
Figure 6:
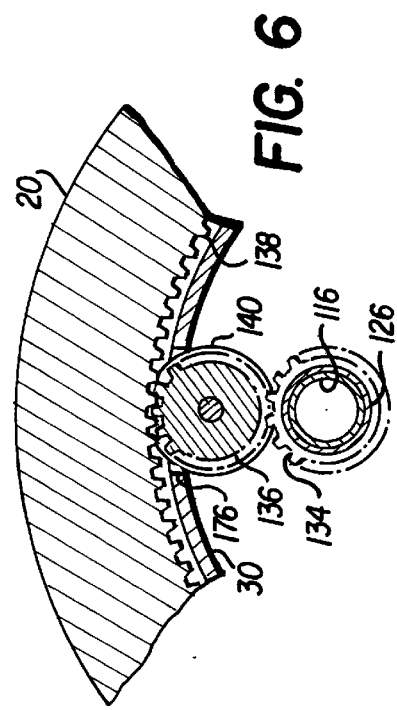
FIG. 6 is a fragmentary cross-sectional view of a needle holder rotating mechanism for use with the suturing instrument according to the present invention taken through line 6—6 in FIG. 5.

The suturing instrument of the present invention can be utilized to suture any type of anatomical tissue in any type of anatomical cavity; and, accordingly, while the instrument is described hereinafter for use with a portal sleeve in endoscopic procedures, such as laparoscopy, the instrument can be used in open surgery and with catheters and other small and large diameter tubular or hollow, cylindrical members providing access to small cavities, such as veins and arteries, as well as large cavities, such as the abdomen.

A suturing instrument 10 in accordance with the present invention, as illustrated in FIGS. 1–6, includes a hub or housing 12, a handle 14 coupled with the housing, an elongate shaft or barrel 16 extending distally from the housing, a needle holder 18 movably disposed within a longitudinal channel formed through the shaft, and a collar 20 disposed distally of the housing along the length of the shaft to control operation of the needle holder in conjunction with the handle.

Figure 4:
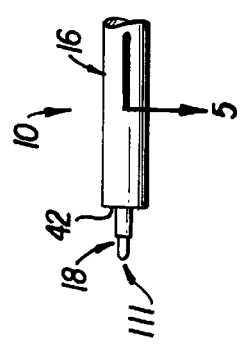
FIG. 4 is an enlarged front view of the distal end of the suturing instrument taken along line 4—4 in FIG. 3B.
Figure 4:
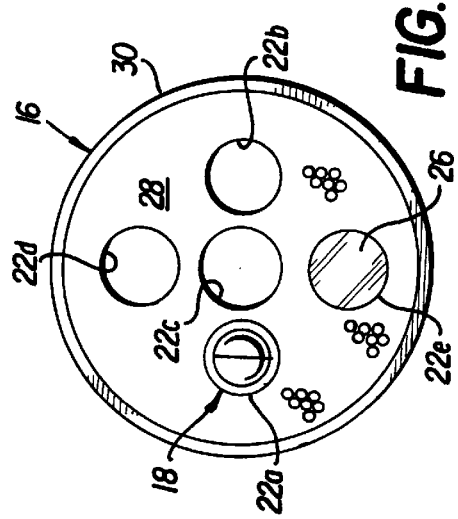

As best seen in FIG. 4, elongate shaft 16 is of generally cylindrical configuration with a plurality of longitudinally extending passages or channels 22a, 22b, 22c, 22d and 22e defined therethrough in spaced, parallel relation, the channels each being of generally circular configuration in transverse cross-section. Channel 22c is disposed coaxial with a central longitudinal axis 24 of the shaft. Channels 22a and 22b are laterally offset from central channel 22c and are disposed on opposite sides of the central channel in diametrically opposed relation. Channels 22d and 22e are laterally offset from central channel 22c and are defined in the spaces between channels 22a and 22b. Needle holder 18 is shown extending through channel 22a, and an endoscope 26 of conventional design is shown extending through channel 22e. Channels 22b, 22c and 22d are shown in an open condition to provide access to an anatomical body cavity from outside the body via the suturing instrument without the need of having to create additional incisions or punctures through the wall of the anatomical cavity. Optical fibers 28 are shown extending through shaft 16 to transmit light from a proximal light source to the body cavity of the patient. The optical fibers are shown extending through a tubular member or sleeve 30 forming the outer surface of the shaft, however, the shaft can be formed without a separate sleeve, for example by embedding or molding the optical fibers within a medically acceptable polymer matrix or by adhesively connecting the fibers together. Channels 22a, 22b, 22c, 22d and 22e can optionally be formed by thin wall, tubular sleeves extending longitudinally through shaft 16 or by voids or spaces defined between the optical fibers as shown.

Figure 2:
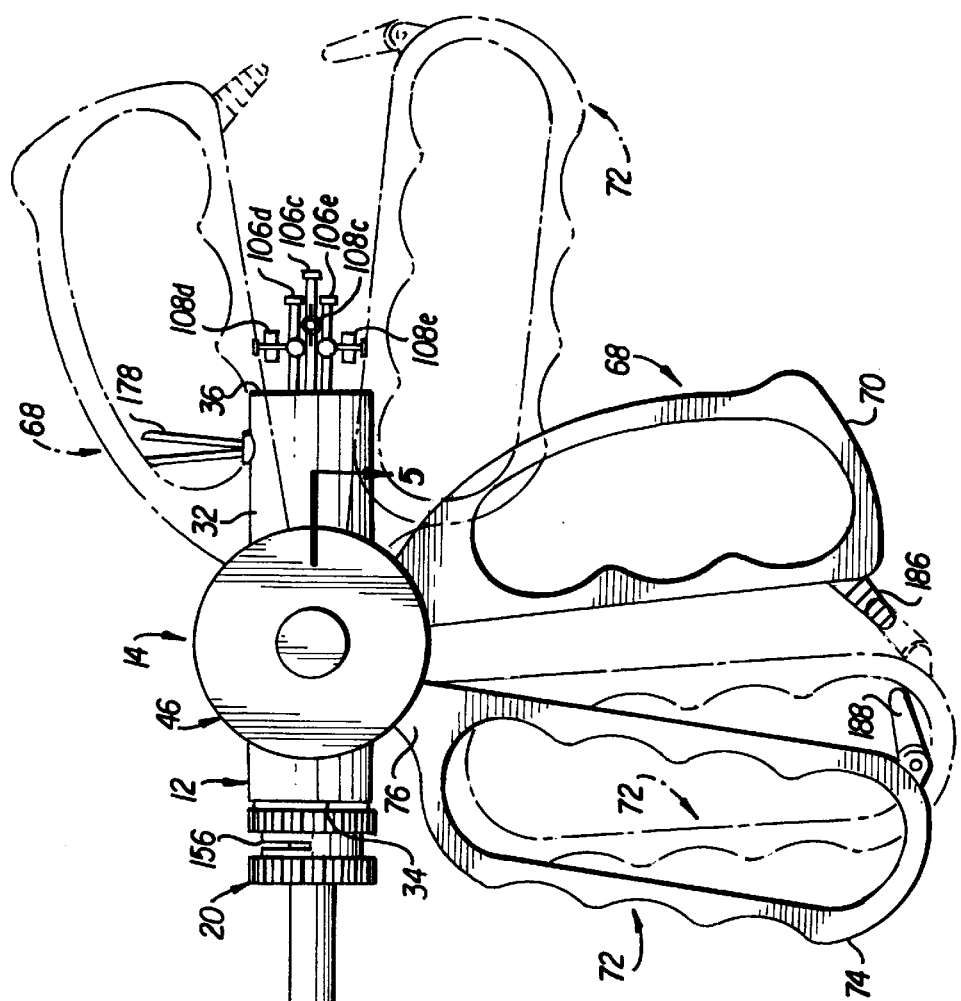
FIG. 2 is a side view, broken longitudinally, of the suturing instrument shown in FIG. 1.
Figure 5:
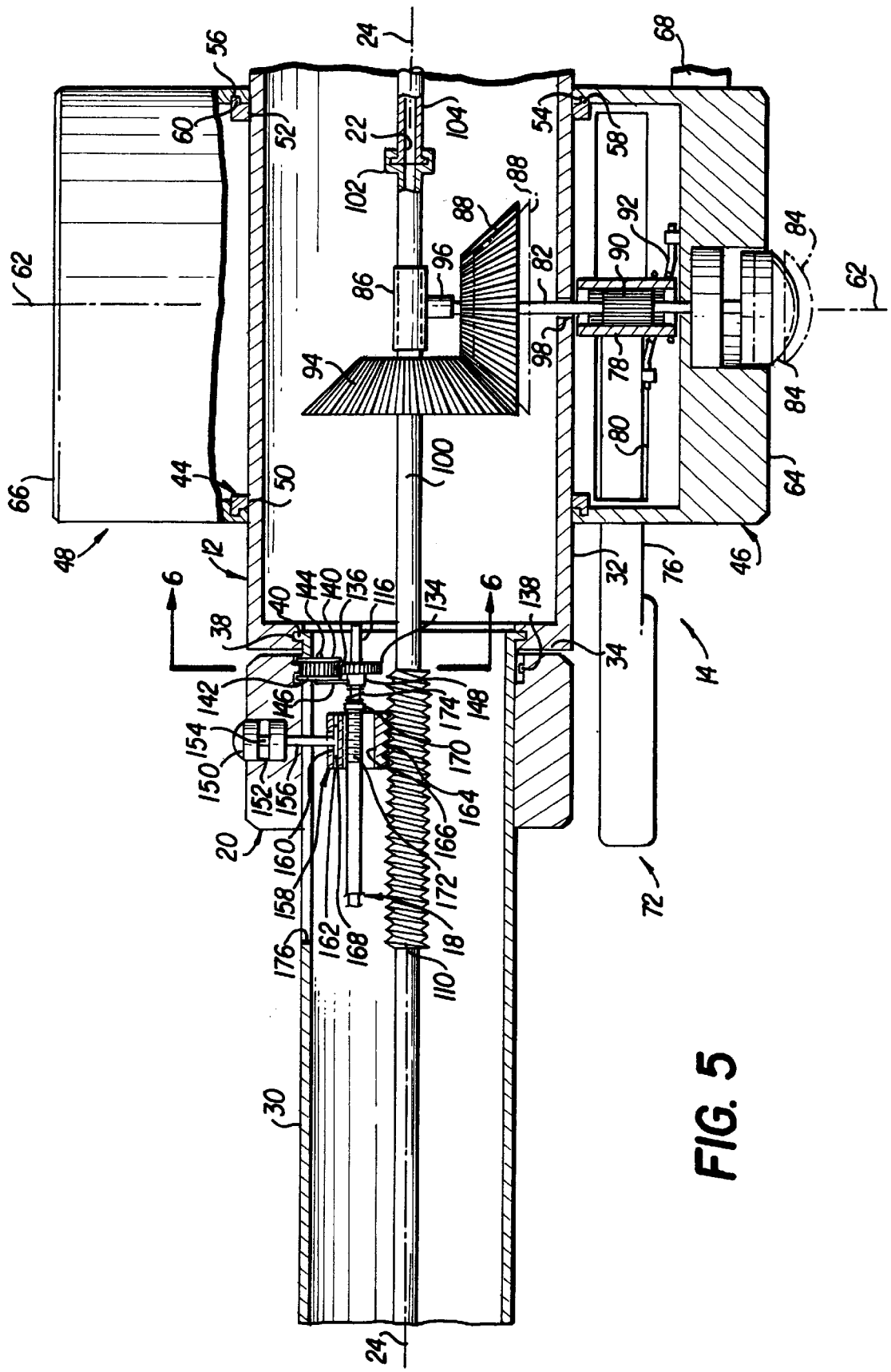
FIG. 5 is a fragmentary top view, partly in section, taken through line 5—5 in FIG. 2.

As best seen in FIGS. 2 and 5, housing 12 includes a hollow, cylindrical portion or side wall 32 with longitudinally spaced front and rear walls 34 and 36 oriented perpendicular to longitudinal axis 24 of the shaft. Tubular member 30 of the shaft extends distally from an outwardly extending flange 38 fixedly mounted within a recess 40 formed in the front wall of housing 12 to a distal end of generally blunt configuration which cooperates with respective distal ends of the optical fibers to define a generally flat surface or face 42 at a distal end of the shaft, the distal face being shown oriented substantially perpendicular to the longitudinal axis of the shaft for purposes of illustration.

Handle 14 includes a central portion 44 of generally cylindrical configuration oriented perpendicular to the longitudinal axis of shaft 16 and a pair of end caps or end portions 46 and 48 of generally cylindrical configuration disposed at opposite axial ends of the cylindrical central handle portion. Central handle portion 44 is of larger diameter than housing 12 and is provided with axially aligned openings or holes 50 and 52 on opposite sides thereof to permit the cylindrical housing to be inserted cross-wise through the cylindrical central handle portion as shown in FIG. 5. Round flanges 54 and 56 extend outwardly from opposite axial ends of the central handle portion and are received within annular grooves 58 and 60 formed along inner surfaces of the cylindrical end caps 46 and 48 adjacent respective open ends of the end caps to permit rotation of the end caps about a central longitudinal axis 62 of handle portion 44. End caps 46 and 48 are of cup-like configuration and extend outwardly from respective open inner ends to outer ends closed by walls 64 and 66, respectively, of generally circular configuration oriented perpendicular to the longitudinal axis 62 of the central handle portion.

A fixed handle member 68 in the form of a finger loop 70 extends downwardly, looking at FIGS. 1 and 2, from the cylindrical side wall of end cap 46 at an acute angle relative to the proximal direction to accommodate one or more fingers of a user's hand. A movable handle member 72 includes a finger loop 74 disposed distally of fixed finger loop 70 and an arm 76 extending upwardly from the finger loop to a terminal end in the form of an internally splined sleeve or collar 78 of generally cylindrical configuration disposed within end cap 46 via an elongate slot 80 formed part way about the circumference of the cylindrical side wall of the end cap adjacent the point of attachment for finger loop 70. A transverse shaft 82 extends through splined sleeve 78 from a push button 84 disposed within a cylindrical recess formed in end cap wall 64 to a tubular sleeve or collar 86 with a smooth bore disposed within housing 12 perpendicular to the shaft. Transverse shaft 82 carries a bevel gear 88 of decreasing diameter in the direction of sleeve 86, the bevel gear being disposed between the smooth bore sleeve and the side wall of the housing. A spur gear 90 is carried on transverse shaft 82 within end cap 46. Spur gear 90 engages straight teeth or splines formed on an inner surface of sleeve 78 parallel to longitudinal axis 62 of the handle so that, among other things, pivotal movement of movable handle member 72 is translated into rotary movement of shaft 82. The movable handle member is preferably biased to move in a counterclockwise direction, looking at FIG. 2, toward fixed handle member 68, for example using a bias member 92 connected between the movable handle member and end cap 46. While a bias member in the form of a torsion spring is shown coiled around sleeve 78 in FIG. 5, it will be appreciated that other types of bias members can be used including, but not limited to, compression or expansion springs, leaf springs, rubber or magnets. Alternatively, the movable handle can be biased away from the fixed handle or configured for ratcheting or frictional movement.

Push button 84 is of a conventional type which, when pressed, alternatingly moves shaft 82 in the axial direction, along longitudinal axis 62 of the handle, between an engaged or depressed position where the first bevel gear 88 engages a second bevel gear 94 as shown by solid lines in FIG. 5 and a disengaged or elevated position, outwardly spaced from the extended position, where the first bevel gear is disengaged from the second bevel gear as shown by broken lines in FIG. 5. Spur gear 90 is disposed within end cap 46 and is of sufficient axial length to permit movement of the shaft in the axial direction while remaining at least partly engaged with splined sleeve 78 at the end of handle member 72. A tubular extension 96 extends radially outward from the smooth bored sleeve in the direction of bevel gear 88 to receive the inner terminal end of shaft 82 telescopically, the tubular extension being sufficiently long to accommodate axial movement of the shaft associated with operation of button 84. Shaft 82 extends through an elongate slot 98 formed part way about the circumference of housing sidewall 32 to permit rotation of handle 14 about the longitudinal axis of housing 12 as described in greater detail below.

Referring still to FIG. 5, second bevel gear 94 is mounted on an elongate drive shaft 100 extending longitudinally through the suturing instrument and is of decreasing diameter in the proximal direction to mesh with first bevel gear 88 when push button 84 is depressed or operated to move the first bevel gear to the engaged position. Drive shaft 100 is of hollow, tubular configuration and is oriented coaxial with longitudinal axis 24 of the suturing instrument to define central channel 22c. The drive shaft extends through smooth bored sleeve 86 to define an axis of rotation for the handle and terminates proximally at a rotational coupling 102 within housing 12 where the drive shaft connects telescopically with a tubular shaft extension 104, the tubular shaft extension preferably being fixed relative to a wall or walls of the housing so that it does not rotate or otherwise move with the drive shaft. Shaft extension 104 extends proximally from coupling 102 through housing rear wall 36 to a coupling 106, for example a Luer-type lock, for connection with sources of fluid or suction, operating units, or medical instruments and devices, with a valve 108 being disposed between the couplings to control passage of fluids and instruments through the central channel. The drive shaft is preferably formed of a medically acceptable plastic or metal material having a wall thickness sufficient to carry or form external threads within shaft 16 as shown at 110 in FIG. 5. As will be described in greater detail below, needle holder 18 is coupled with threaded portion 110 of the drive shaft such that handle members 68 and 72 can be used to control operation of its needle holding members.

Figure 3A:
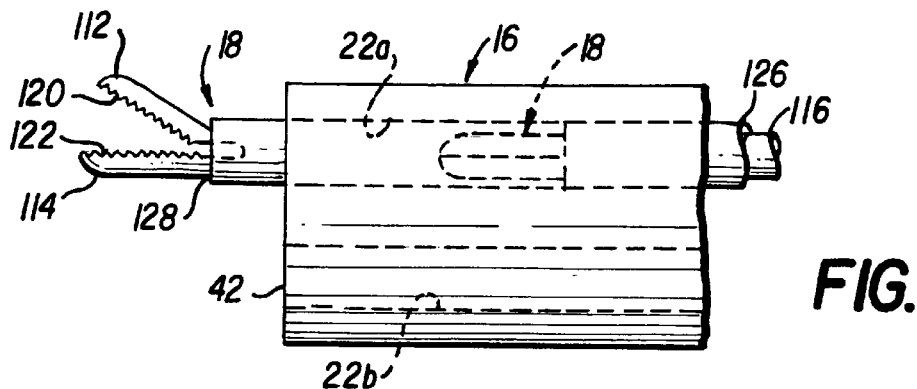
FIG. 3A is a fragmentary top view of the distal end of the suturing instrument shown in FIG. 2 with the needle holder in an axially retracted, open position.

Needle holder 18 includes a pair of cooperating needle holding members 112 and 114 mounted by the housing for rotation, defining a needle holding portion, the needle holding members being movable relative to one another to selectively grasp and release a suture needle or other objects during suturing procedures. Needle holding members 112 and 114 of the needle holder are shown as a pair of pivotally opposed jaws in FIGS. 3A and 3B but can have other configurations for grasping and releasing a suture needle as well as for performing other functions during a surgical procedure. Jaws 112 and 114 are preferably formed at the distal end of an elongate tubular rod or body 116 as an integral one-piece unit; however, it will be appreciated that the jaws can be formed separately from the tubular rod and attached thereto and that the tubular rod can be of solid configuration in cross section, if desired. As shown, however, the tubular needle holder rod 116 defines an elongate passage 118 through the needle holder which can be used as an additional or auxiliary operating channel providing access to the operative site from outside the body. Preferably, the tubular needle holder rod 116 will terminate proximally at a coupling (not shown) similar to coupling 106 and will be provided with a valve (not shown) disposed distally of the coupling to control access through the operating channel 118 of the needle holder. The jaws of the needle holder are preferably biased apart toward an open position, shown in FIG. 3A, where inner needle holding or grasping surfaces 120 and 122 are angularly spaced from one another. The lower jaw 114 in FIG. 3A is of fixed configuration and extends in parallel with a longitudinal axis 124 at the distal portion of the needle holder while the upper jaw 112 is pivotally movable between an open position, shown in FIG. 3A, where it extends outwardly from the longitudinal axis 124 of the needle holder distal portion at an angle and a closed position, shown in FIG. 3B, where it is in substantially parallel, abutting relation with the lower jaw. Opposed inner surfaces 120 and 122 of the jaws are shown with a plurality of longitudinally spaced teeth or ribs oriented perpendicular to the longitudinal axis 124 of the needle holder distal portion to securely hold a suture needle, tissue or other objects therebetween during a surgical procedure; however, the inner surfaces can have any suitable configuration for holding a suture needle and performing other functions including, but not limited to, configurations made up of spaced diamond-shaped protrusions, irregularly spaced teeth or ribs, and opposed arcuate portions which define a hole or opening when closed. As will be described in greater detail below, either jaw can carry a cutting member or biopsy box.

Figure 3B:
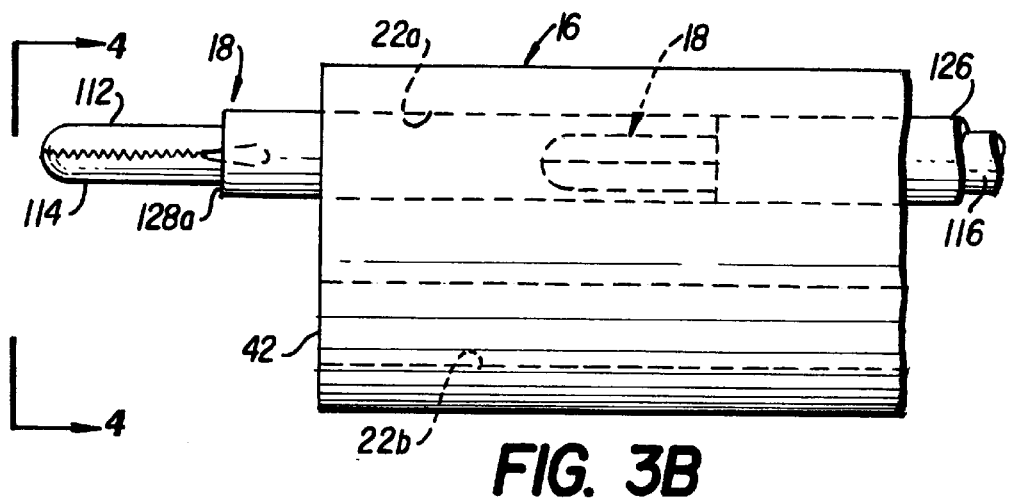
FIG. 3B is a fragmentary top view of the distal end of the suturing instrument shown in FIG. 2 with the needle holder in an axially retracted, closed position.

Referring to FIGS. 3A, 3B and 4, it can be seen that fixed jaw 114 of the needle holder is disposed between movable jaw 112 and central channel 22c so that, when the jaws of the needle holder are open, they will not interfere with instruments inserted through the other operating channels. Under certain circumstances, however, it may be desirable to orient the needle holder in a manner causing the movable jaw to be disposed inwardly of the fixed jaw, for example, by rotating the jaws 180° from the positions shown in FIG. 4. The tubular body or rod 116 of needle holder 18 is disposed telescopically within a flexible elongate outer member or sleeve 126 of tubular configuration which is axially movable relative to the rod between a retracted position, shown in FIG. 3A, where a distal end 128 of the flexible sleeve is proximally spaced from the jaws to allow them to open under the force of their own resilience and an extended position, shown in FIG. 3B, where the distal end of the flexible outer member slides over the jaws to cause them to close. The rod 116 and sleeve 126 of the needle holder cooperate to define an elongate proximal portion 130 of generally straight configuration extending through channel 22a in shaft 16 and a distal arm portion 132 with a predetermined deployed or working shape or condition where the distal portion bends outwardly at an angle relative to the longitudinal axis 125 of the proximal portion of the needle holder, the distal portion assuming the deployed shape or condition when the needle holder is in an axially extended position with the distal portion protruding distally beyond the distal end or face 42 of the shaft as shown, for example, in FIGS. 7 and 8. The length and angular deflection of the distal portion of the needle holder are such that at least portions of jaws 112 and 114 are spaced laterally outward of a peripheral edge or diameter of the shaft 16 when the distal portion of the rod is in the deployed condition. Preferably, the distance between the axis of rotation 125 of the proximal portion of the needle holder and the position of needle holding surfaces 120 and 122 is approximately equal to the radius of curvature of the suture needle to be used so that the suture needle can be held between the needle holding surfaces and driven through anatomical tissue along an arcuate path having a radius of curvature substantially commensurate with the needle radius of curvature to minimize tissue trauma. The tubular rod is preferably stiffer than the sleeve but formed of an elastic material or with an elastic portion having elastic properties allowing the distal portion to bend inwardly, in a lateral direction relative to the longitudinal axis of the proximal portion of the rod so that, when the rod is axially retracted or moved proximally relative to the shaft, the distal portion will move laterally inward from the deployed working position shown in FIGS. 7 and 8 to the undeployed insertion position shown in FIGS. 1 and 2. In the axially retracted position, a sufficient amount of the distal portion of the needle holder is disposed within the shaft to cause the distal portion to straighten out or assume an undeployed shape or condition where the jaws do not protrude beyond the outer periphery or diameter of the shaft. If desired, however, the instrument can be modified to permit complete retraction of the needle holder to a position where the jaws are proximally spaced from the distal end or face of the shaft as shown, for example, by broken lines in FIGS. 3A and 3B.

Tubular rod 116 of needle holder 18 carries a spur gear 134 adjacent a proximal end of collar 20, the spur gear having straight teeth oriented parallel to longitudinal axis 125 of the proximal portion of the needle holder. An idler gear 136 is disposed between spur gear 134 and a sun gear 138 of epicyclic configuration formed along an inner surface of collar 20 adjacent the proximal end of the collar. Idler gear 136 includes a pair of face plates 140 and 142 of circular configuration which extend radially beyond the gear teeth to define a pair of lips or rims between which the spur gear and the epicyclic collar gear are disposed in order to maintain alignment of the gear system. Idler gear 136 is mounted on a pin 144 secured to a plate 146 extending upwardly, looking at FIG. 5, from the distal end of a tubular spacer 148 disposed telescopically around rod 116 adjacent spur gear 134.

A push button 150 is disposed within a cylindrical recess 152 formed in an outer surface of collar 20 and includes a plunger or post 154 extending from the button through an elongate slot 156 formed part way about the circumference of the collar to a linear coupling block 158 disposed within shaft 16. Plunger 154 extends through a longitudinal slot 160 formed in block 158 to a cross member 162 wider than the slot so as to allow the block to slide transversely relative to the plunger while remaining attached to the plunger. Block 158 carries one or more external teeth 164 on a side facing threaded portion 110 of drive shaft 100 and defines a longitudinal opening or passage 166 therethrough with internal teeth 168 formed on an upper surface thereof looking at FIG. 5. The block is movable by operation of the button between an engaged position where teeth 164 meshingly engage threaded portion 110 of the drive shaft to cause the block to move linearly in response to rotation of the shaft and a disengaged position where the teeth 164 are radially or laterally spaced from the threaded portion such that the block is not moved in response to rotation of the shaft.

The outer tubular sleeve 126 of needle holder 18 extends through opening 166 in block 158 with lateral clearance and includes a round flange 170 extending radially outward therefrom between the block and spacer 148 and a rack made up of axially spaced rings or teeth 172 that extend around the portion of the sleeve disposed within the longitudinal block opening. Teeth 172 of the rack meshingly engage teeth 168 on the inner surface of the block opening when block 158 is in the engaged position shown in FIG. 5 such that axial movement of the block caused by rotation of shaft 100 is imparted to needle holder sleeve 126 thereby controlling the operation of jaws 112 and 114 as will be described in greater detail below.

A bias member 174 is disposed between spacer 148 and flange 170 to bias sleeve 126 distally relative to rod 116 so that jaws 112 and 114 are normally in a closed position. The bias member is shown as a helical spring coiled around rod 116 and held in compression between flange 170 and spacer 148, however, any suitable bias member can be used including, but not limited to, tension springs, compression springs, helical springs, leaf springs, rubber and magnets.

Referring still to FIG. 5, idler gear 136 and plunger 154 extend through a longitudinal slot 176 formed through tubular member 30 of the shaft to permit axial movement of the collar assembly when push button 150 is operated to move block 158 to a disengaged position such as the position of block 158 shown by broken lines in FIG. 5. Preferably, collar 20 will slide frictionally against or be coupled in ratching relation to shaft 16 so that, once the collar is moved to a desired axial location relative to the shaft, the collar will not move unless deliberately forced. If desired, a separate locking mechanism can be provided to maintain the axial and/or angular location of the collar relative to the shaft while permitting the collar to rotate about the longitudinal axis 24 of the shaft.

An electrical connector can optionally be mounted on the housing 12, as shown at 178 in FIG. 1, or at any other suitable location on the instrument including, but not limited to, the instrument handle or the proximal end of one of the channel-defining tubular shafts extending proximally from the housing, to connect electrically conductive elements of the instrument with a source of electricity for performing unipolar or bipolar procedures such as electric coagulation, for example using one or both of the jaws of the needle holder as conductive elements. In addition, an interior surface of any of the channels 22_a_ - 22_e_ can be coated with an electrical and/or thermal insulating layer to permit safe insertion of electrical, thermal and/or other types of energy transmitting devices through the operating channels.

In use, instrument 10 is preferably grasped using finger loops 70 and 74 and, in the case of an endoscopic procedure, the instrument is guided to the operative site by a portal sleeve positioned in the wall of an anatomical cavity. The portal sleeve can be positioned in the anatomical cavity wall using any suitable penetrating technique, including those creating puncture sites by means of removable obturators, such as trocars, and can include a valve housing, if desired, to prevent loss of pneumoperitoneum during insertion and withdrawal of the instrument. The visualization of the endoscopic procedure can be accomplished using a conventional endoscope incorporated into the instrument, for example within the longitudinal operating channel 22_e_ defined through shaft 16, or separately positioned within the anatomical cavity through a second portal sleeve located at another puncture site.

Prior to insertion, instrument 10 is preferably in the condition, state or position shown in FIGS. 3B and 4. More specifically, needle holder 18 is preferably initially in an axially retracted position where a distal portion of the needle holder is drawn at least part way into elongate shaft 16 and thus forced to move laterally inward in an elastic manner to an undeployed position where the needle holder jaws are spaced laterally inward of the peripheral edge of the shaft so as not to snag or catch on structure within the portal sleeve or valve housing during insertion. To this end, collar 20 is preferably initially disposed in the retracted position shown in FIG. 2 with plunger 154 being disposed at the proximal ends of slot 176 in the shaft. Push button 150 on collar 20 is preferably initially disposed in an elevated position so that the jaws of the needle holder will be in a closed or grasping position with inner grasping surfaces of the jaws close together or abutting one another. Alternatively, or in addition to the above, a sheath (not shown) can be telescopically fitted around the elongate tubular member or shaft in a manner to be movable axially or longitudinally between a retracted position spaced proximally of the end effectors and an extended position protruding distally from the shaft to cover and protect the end effectors.

Figure 8:
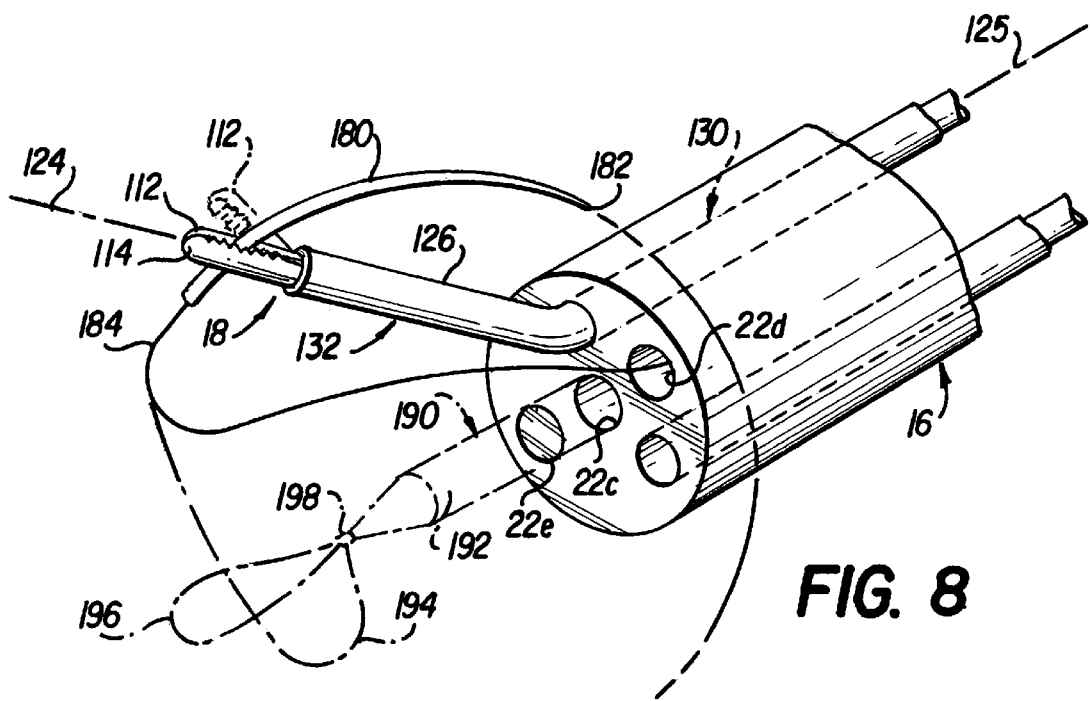
FIG. 8 is a fragmentary perspective view of the distal end of the suturing instrument shown in FIG. 7.

After insertion, needle holder 18 is preferably moved distally relative to shaft 16 from the axially retracted, undeployed position shown in FIG. 3B to the axially extended, deployed position shown in FIGS. 7 and 8 by sliding collar 20 distally along longitudinal slot 176. As the needle holder is advanced longitudinally, the distal portion of the needle holder will no longer be restrained within the channel of the elongate shaft and will thus tend to recover elastically or move toward an undeformed shape or condition. More particularly, the distal portion of the needle holder will spread apart or bend outwardly, away from the longitudinal axis of the channel from which it extends, toward a deployed position where the jaws of the needle holder are spaced laterally outward of the peripheral edge of the shaft.

A curved suture needle 180, preferably having a radius of curvature substantially commensurate with the distance between the axis of rotation of needle holder 18 and the deployed position of the needle holder, is positioned in the needle holder by moving jaws 112 and 114 apart from the closed position shown by solid lines in FIG. 8 to the open position shown by broken lines in FIG. 8, placing the body of the suture needle in the space between the jaws, and moving the jaws toward the closed position until grasping surfaces 120 and 122 of the needle holder abut the suture needle to hold it firmly in place.

Jaws 112 and 114 are moved to the open position by operation of handle members 68 and 72. If push button 84 of the handle is in the elevated or disengaged position shown by broken lines in FIG. 5, the push button is depressed to cause bevel gear 88 to move inwardly, in the direction of longitudinal axis 24, and into meshing engagement with bevel gear 94 mounted on drive shaft 100, as shown by solid lines in FIG. 5. Movable handle member 72 is then moved in a clockwise direction, looking at FIG. 2, away from fixed handle member 68 to cause internally threaded sleeve 78 to rotate in a clockwise direction. Spur gear 90 rotates with sleeve 78, causing shaft 82 to rotate in the clockwise direction with bevel gear 88. Bevel gear 94 is thus rotated in a counterclockwise direction, looking proximally, causing drive shaft 100, including threaded portion 110, to rotate in a counterclockwise direction. Rotation of the drive shaft 100 can be converted into linear movement of the needle holder components by selectively depressing button 150 mounted on collar 20. Depression of the button causes block 158 to move inwardly, toward the drive shaft, such that teeth 164 mesh with or engage the threaded portion 110 of the drive shaft. Coupling block 158 moves linearly in the proximal direction along the drive shaft as the drive shaft rotates in the counterclockwise direction, with the plunger 154 sliding axially within slot 160 formed through the block. In the depressed or engaged condition shown at the top of FIG. 5, the teeth or rings 172 of the needle holder sleeve 126 engage teeth 168 inside the block opening 166 such that the needle holder sleeve 126 moves linearly with the block in the proximal direction relative to rod 116. The distal end 128 of the sleeve 126 is thus moved proximally relative to the jaws, allowing the jaws to spread apart or move toward the open position shown in FIG. 3A under the influence of their own elasticity or resilience. The needle 180 is then placed between grasping surfaces 120 and 122 of the needle holder with the body of the needle being oriented transverse to the longitudinal axis of the distal portion of the needle and, preferably, coaxial with the axis of rotation of the needle holder. With needle 180 positioned between jaws 112 and 114 of needle holder 18, movable handle member 72 is released or otherwise caused to move in a counterclockwise direction, looking at FIG. 2, in response to finger pressure and/or the spring bias provided by bias member 92. As the movable handle member 72 moves counterclockwise, transverse shaft 82 is also caused to move counterclockwise thereby carrying bevel gear 88 in the counterclockwise direction. Bevel gear 94 is thus caused to move in a clockwise direction, looking proximally along longitudinal axis 24, so that drive shaft 100 is driven clockwise, causing block 158 to move in the distal direction relative to rod 116 such that distal end 128 of the sleeve moves distally relative to the rod and into camming contact with the jaws 112 and 114, causing the jaws to move toward one an other and into gripping contact with the body of needle 180 as shown by solid lines in FIG. 8. Needle 180 is thus held securely between jaws 112 and 114 and will move with the needle holder 18 during the suturing procedure. If the force biasing the jaws to a closed position is not sufficient to hold a suture needle between the jaws in a desired positioned during suturing procedures, finger loops 70 and 74 can be squeezed tightly together and locked in place by ratchet members 186 and 188 mounted in opposed relation on the handle members.

Figure 9:
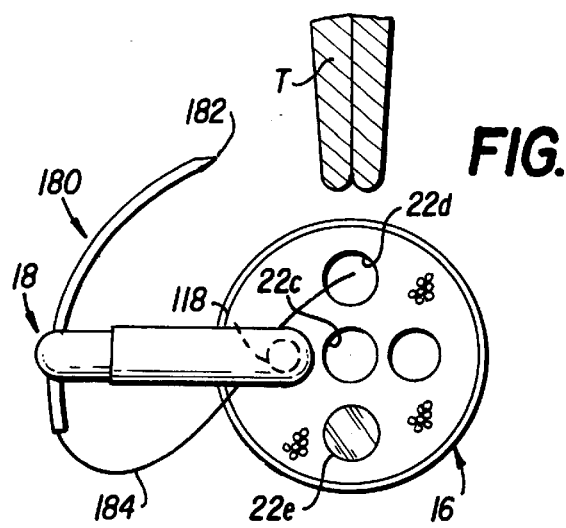
FIGS. 9–12 are front views of a suturing instrument illustrating a method of suturing anatomical tissue in accordance with the present invention.
Figure 10:
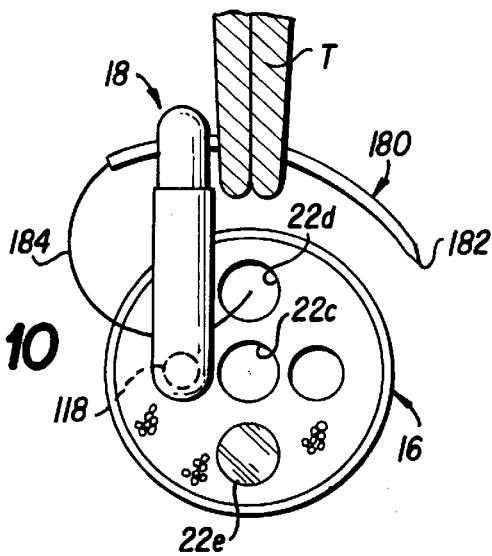

At this point, tip 182 of needle 180 is positioned adjacent anatomical tissue T as shown in FIG. 9. For purposes of illustration only, a length of filamentous suture material 184 is shown extending from one of the operating channels to the proximal end of the needle. Needle 180 is driven through tissue T by rotating collar 20 in a counterclockwise direction, looking at FIG. 6, so that idler gear 136 is also moved in a counterclockwise direction to drive spur gear 134 in a clockwise direction. Clockwise movement of spur gear 134 causes the proximal portion of needle holder 18 to rotate clockwise within channel 22a such that jaws 112 and 114 at the distal end of the needle holder are caused to move along a first arcuate path coaxial with longitudinal axis 125 of the proximal portion but having a radius of curvature approximately equal to or substantially commensurate with the radius curvature of the needle until the tip 182 of needle 180 is caused to penetrate through the anatomical tissue T and be disposed at a location on the opposite side of the tissue as shown in FIG. 10.

Figure 11:
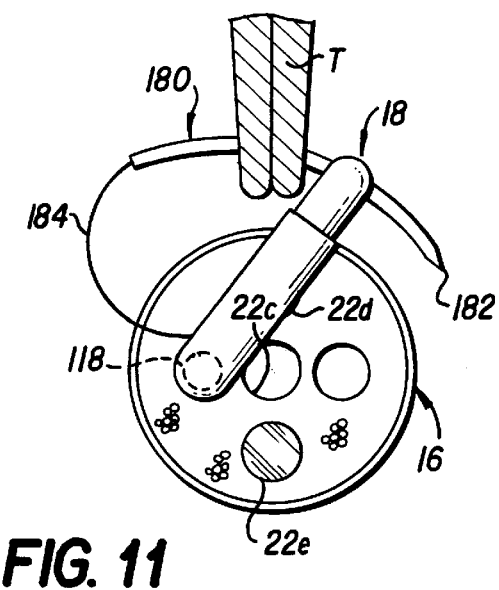

Needle holder jaws 112 and 114 are then opened by pushing button 150 on collar 20 to cause block 158 to engage threaded portion 110 of drive shaft 100 and by moving handle member 72 in a clockwise direction, looking at FIG. 2, away from fixed handle member 68. As described above, clockwise rotation of handle member 72 causes drive shaft 100, including threaded portion 110, to rotate in a counterclockwise direction. Coupling block 158 moves linearly in the proximal direction along the drive shaft as the drive shaft rotates in the counterclockwise direction, causing needle holder sleeve 126 to move linearly with the block in the proximal direction relative to rod 116. The distal end 128 of the sleeve 126 is thus moved proximally relative to the jaws, allowing the jaws to spread apart or move toward the open position shown in FIG. 3A under the influence of their own elasticity or resilience. The suture needle 180 is thus released from the jaws of needle holder 18 but is held in place within tissue T due to friction and the tendency of the tissue to resist further penetration. Needle holder 18 is then rotated in a counterclockwise direction, looking at FIG. 10, from the position where the needle is released to a pick-up position on the other side of the tissue as shown in FIG. 11. Counterclockwise rotation of the needle holder can, for example, be accomplished by rotating collar 20 in a clockwise direction, looking proximally, to cause idler gear 136 to be driven in a clockwise direction by sun gear 138 and spur gear 134 to be driven in the counterclockwise direction. If the instrument is held relatively stationary as the collar is rotated, the needle holder can be accurately repositioned with minimum adjustment by the user, particularly when the arcuate movement of the needle holding members is predefined to correspond to or be commensurate with the needle radius of curvature.

Figure 12:
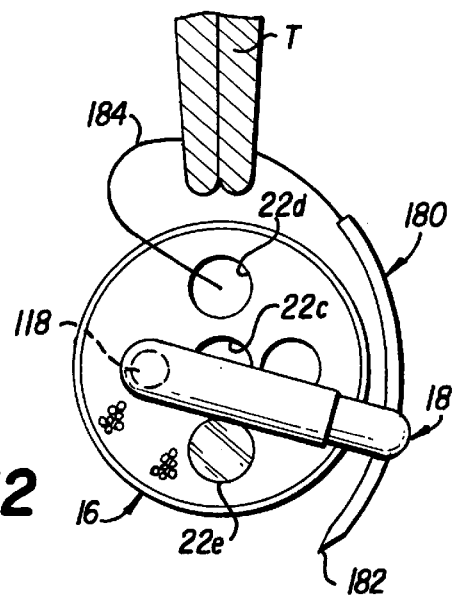

When suture needle 180 is disposed between jaws 112 and 114 of the needle holder, finger pressure on handle members 68 and 72 is reduced to allow bias member 92 to move needle holder sleeve 126 distally to close the jaws. Button 150 on collar 20 can be pushed to disengage block 158 from threaded portion 110 of drive shaft 100, if desired. The needle holder 18 is then rotated in a clockwise direction, as shown in FIG. 12, to pull the suture needle 180 through the tissue T along an arcuate path coaxial with longitudinal axis 125 of the needle holder and having a radius of curvature approximately equal to or substantially commensurate with the radius of curvature of the needle to minimize tissue trauma. At this point, the length of suture material 184 can be knotted to form a single stitch or another stitch can be made by performing the above steps at a second site or location in the manner described above. In the latter technique, the suture needle 180 may need to be advanced circumferentially in the clockwise direction in order for the tip 182 to protrude sufficiently from the needle holder for additional stitches to be formed. Such repositioning can, for example, be accomplished by grasping the proximal end of the needle with a separate needle holding instrument and releasing the needle holding members of the needle holder to allow manipulation of the needle to a position in the needle holder wherein the tip of the needle protrudes sufficiently to pass through the anatomical tissue.

Figure 13:
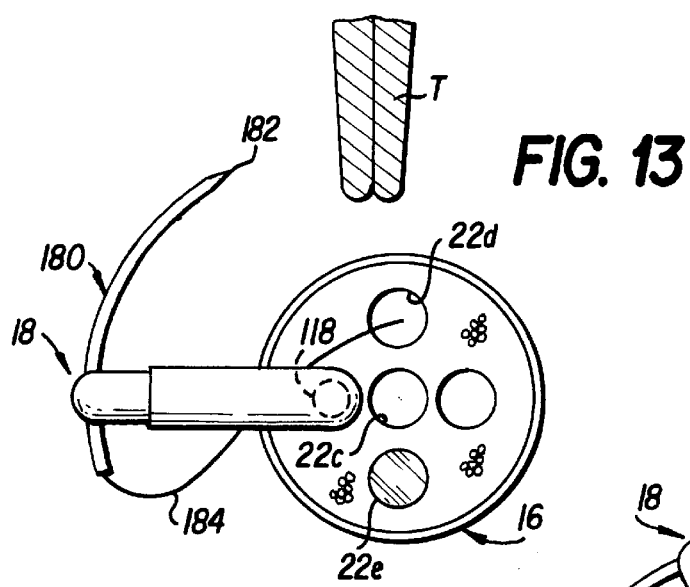
FIGS. 13–16 are front views of a suturing instrument illustrating another method of suturing anatomical tissue according to the present invention.
Figure 14:
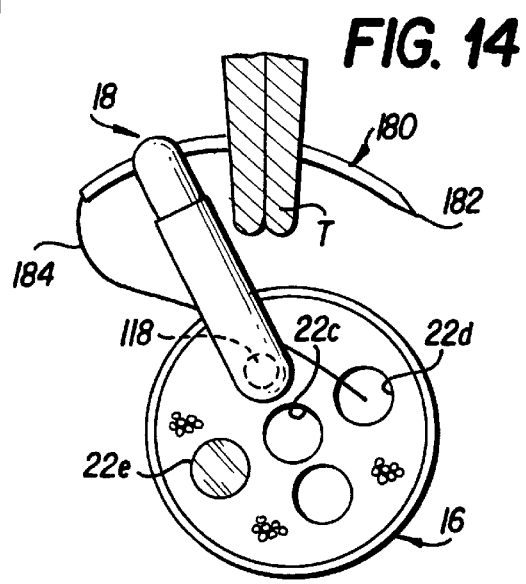
Figure 15:
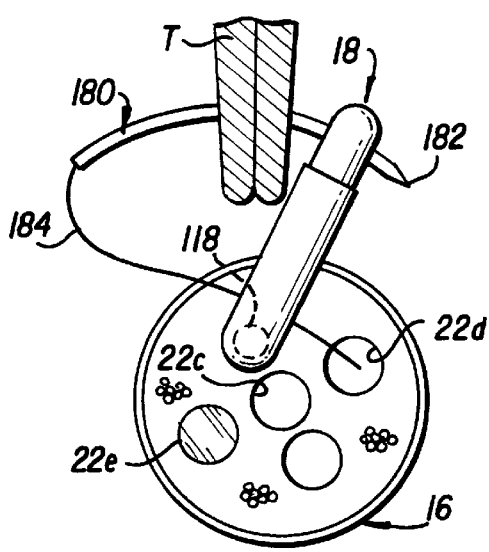
Figure 16:
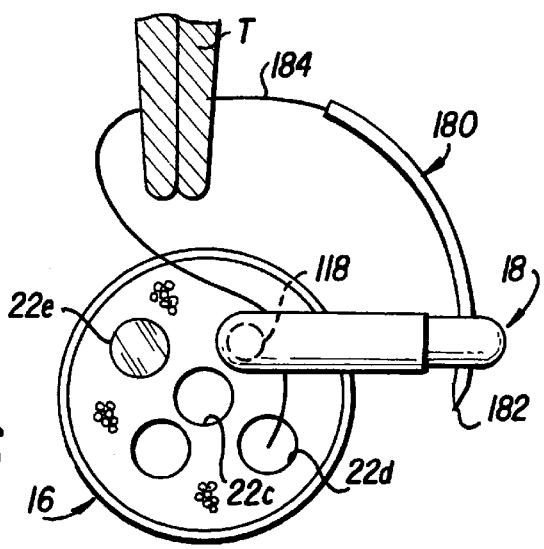

The suturing instrument can also be used to suture anatomical tissue in the manner shown in FIGS. 13–16 wherein suture needle 180 is initially held between jaws 112 and 114 as shown in FIG. 13, either with button 150 engaged and handle members 68 and 72 squeezed or locked together, or with button 150 disengaged so that the suture needle is held between the jaws of the needle holder under the influence of the force biasing the needle holder jaws together. Tip 182 of the needle is positioned adjacent tissue T, after which shaft 16 is rotated in a clockwise direction, looking at FIG. 13, about the longitudinal axis 24 of the shaft, for example by rotating handle 14 with a twisting movement of the user's wrist and allowing the instrument housing to rotate with the handle, to drive the suture needle 180 through tissue T in a clockwise direction as shown in FIG. 14, preferably along an arcuate path having a radius of curvature substantially commensurate with the radius of curvature of the needle. The jaws of the needle holder are then opened in the manner described above, and the needle holder is moved counterclockwise, looking at FIG. 14, in an arcuate manner to receive the body or tip of the suture needle, for example by rotating collar 20 in a clockwise direction relative to the shaft while holding the instrument stationary, as shown in FIG. 15. Handle members 68 and 72 are then operated to close the jaws of the needle holder against suture needle 180 so that the suture needle is securely held by the needle holder, after which the needle holder is rotated clockwise to pull the suture needle through the tissue, for example by rotating shaft 16 about longitudinal axis 24 as shown in FIG. 16 or by use of collar 20. The instrument may then be moved slightly to apply another stitch to the anatomical tissue in the manner described above.

At any point during the surgical procedure, operating channels 22a–22e can be used for irrigation or aspiration of the surgical site and can serve as a space for holding the suture material or as a portal for the introduction of other medical instruments and devices such as, for example, forceps, cutting members, needles and endoscopes. Knotting elements can also be introduced at the operative site via the operating channels for use in leu of or in addition to traditional knotting techniques during the suturing procedure. Some examples of suitable knotting elements for this purpose are described in pending applications Ser. Nos. 08/366,285, filed Dec. 29, 1994; 08/377,723, filed Jan. 25,1995; 08/401,002, filed Mar. 9, 1995; and 08/585,875, filed Jan. 16, 1996; the disclosures of which are incorporated herein by reference.

FIG. 8 illustrates a further use of one of the operating channels 22a–22e wherein a ligating device, shown by broken lines at 190, is advanced distally through one of the channels, for example central channel 22c, to assist in tying a suture. The device 190 is of the conventional ENDOLOOP-type and includes an elongate tubular pusher 192 and a length of filamentous ligature material 194 extending through the pusher to define a loop 196 with a knotting element 198 in the form of a pretied knot at the distal end of the pusher. For purposes of illustration, a free end of the ligature material is shown attached to the proximal end of suture needle 180 so that, after the suture needle has been pulled through anatomical tissue with the ligature material, the needle can be passed through the loop and the loop can be tightened to control the tension of the suture.

In addition to operating channels 22a–22e, an auxiliary operating channel can be defined through needle holder 18 as shown by broken lines at 118 in FIGS. 9–16 to provide access to the operative site from outside the anatomical cavity. The auxiliary operating channel can terminate distally at an opening adjacent the jaws of the needle holder or at an opening defined at the bend connecting straight and angled portions of the needle holder.

It will also be appreciated that when push button 84 is in the elevated, undepressed position shown by broken lines in FIG. 5, shaft 82 slides outwardly within tubular extension 96, moving bevel gear 88 away from bevel gear 94 so that end cap 46 may be rotated about an axis transverse to the longitudinal axis of shaft 16 to move handle members 68 and 72 between the transverse position shown by solid lines in FIG. 2 and the rearward facing position shown by broken lines in FIG. 2. Push button 84 may then be depressed to maintain the handle members in the desired angular orientation. The handle members 68 and 72 can also be rotated about the longitudinal axis of the shaft 16 by moving push button 84 to the elevated, undepressed position and rotating the entire handle portion 14 about the housing 12, for example by grasping the housing with one hand while moving the handle with the other hand. When a desired angular orientation is achieved, push button 84 may be depressed so that the bevel gear 88 is made to engage bevel gear 94, thereby locking the handle in place relative to the housing.

While operation of the needle holder has been described above as being controlled by operating mechanisms such as push buttons and collars which, for the most part, must be operated with both hands, it will be appreciated that a single operating mechanism can be used to synchronize movement of the needle holder as well as operation of the needle holding members to further simplify the suturing process by allowing one-hand operation of the instrument. For example, the mechanism described and shown in patent application Ser. No. 08/877,764, filed Jun. 17, 1997, the disclosure of which is incorporated herein by reference, can be simply modified for use with a single needle holder.

Figure 17:
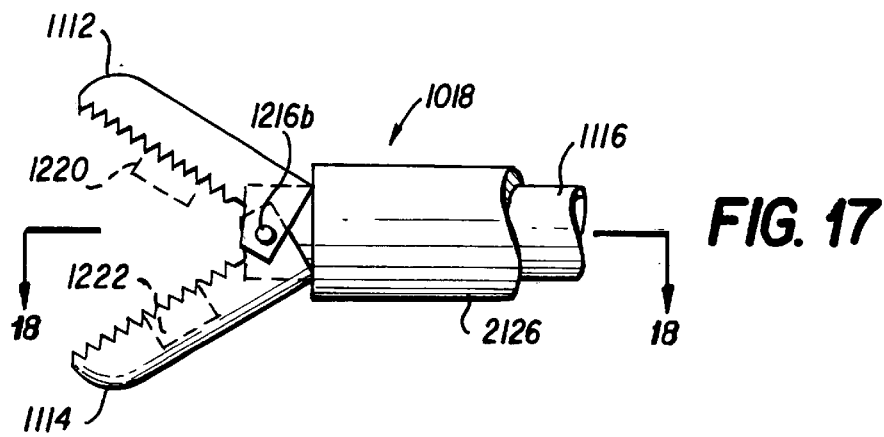
FIG. 17 is a fragmentary side view of a modified needle holder for use with the suturing instrument according to the present invention.
Figure 18:
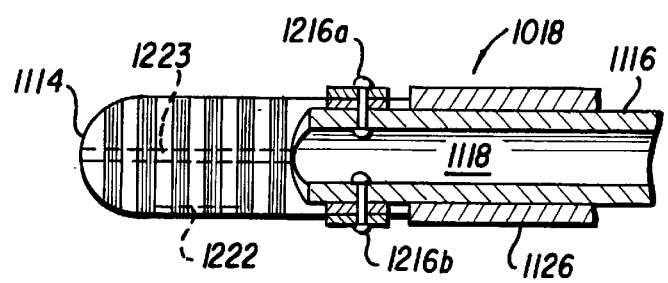
FIG. 18 is a cross-sectional view of the modified needle holder of FIG. 17 taken through line 18—18.

FIGS. 17 and 18 show a modification of a needle holder for use with the suturing instrument according to the present invention wherein the modified needle holder 2118 includes a pair of jaws to 1112 and 1114 pivotably mounted on a pair of pins 1216a and 1216b secured to diametrically opposed sides of a hollow tubular rod or sleeve 1116 telescopically fitted within an outer tubular sleeve 1126, the tubular rod defining an auxiliary operating channel 1118 providing access to the operative site from outside the anatomical cavity. Jaws 1112 and 1114 are biased apart toward the open position shown in FIG. 17, for example using a torsion spring (not shown) coiled around one of the pins and connected between the jaws or a pair of spring members (not shown) held in compression between each jaw and the hollow tubular rod, and the jaws are movable inwardly toward one another against the spring bias in response to distal movement of outer tubular sleeve 1126 against the rear or back edges of the jaws. If desired, jaws 1112 and 1114 can be mounted on a single pin or pivot extending diametrically across the width of sleeve 1116; however, use of separate pivots provides a substantially unobstructed passage through the operating channel.

Any of the needle holding members described herein can carry a biopsy box or a cutting member such as the blade shown by broken lines at 1220 in FIG. 17. Blade 1220 is oriented perpendicular to the inner grasping surface of upper jaw 1112 and extends downwardly, looking at FIG. 17, from the inner grasping surface to fit within a cooperatively configured pocket or recess 1222 formed in lower jaw 1114 when the jaws are closed together. An elongate groove or recess with an open proximal end can be formed along an inner surface of one or both of the jaws, for example as shown by broken lines at 1189 in FIG. 18, to permit a cutting member, such as a blade, to slide between the jaws when closed. Examples of other cutting members which can be used are shown and described in U.S. patent application Ser. No. 08/612,634, filed Mar. 4, 1996, and Ser. No. 08/376,186, filed Jan. 20, 1995, the disclosures of which are incorporated herein by reference.

Figure 19:
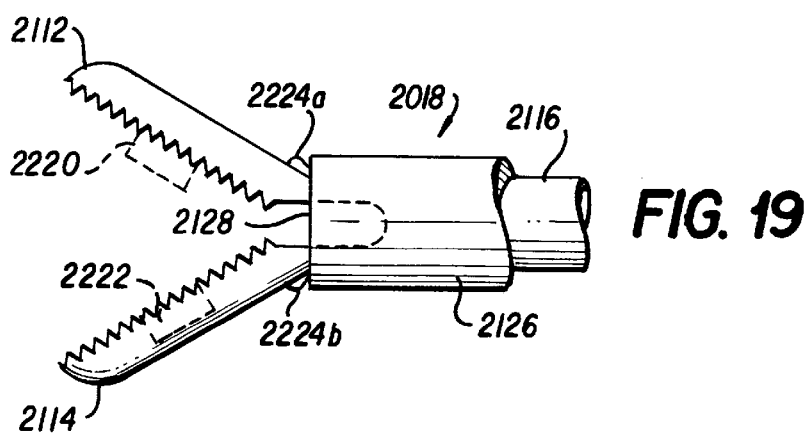
FIG. 19 is a fragmentary side view of another modification of a needle holder for use with the suturing instrument according to the present invention.

The modified needle holder 3018 shown in FIG. 19 is similar to the needle holders shown in FIGS. 1–16 but with both jaws 2112 and 2114 being pivotably movable between normally open positions extending laterally outward from the tubular rod 2116 at acute angles and closed positions wherein the jaws abut one another. A pair of cams 2224a and 2224b are also shown extending outwardly from the jaws adjacent the distal end 2128 of outer sleeve 2126 to provide additional force when closing the jaws together. An optional cutting member in the form of a blade 2220 and a cooperatively configured pocket or recess 2222 are also shown.

Figure 20:
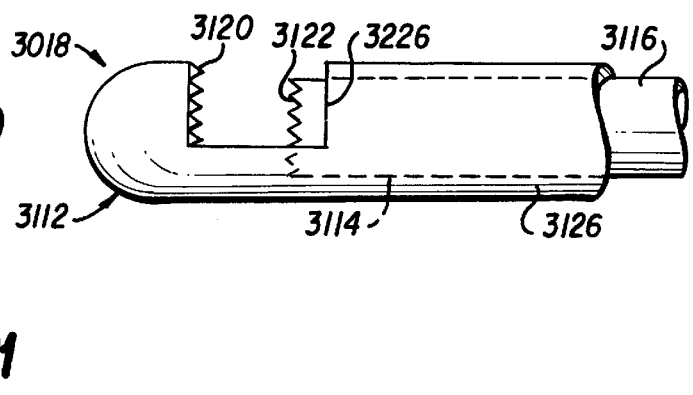
FIGS. 20 and 21 are a fragmentary side view and a front view, respectively, of yet another modified needle holder for use with the suturing instrument according to the present invention.
Figure 21:
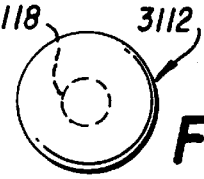

Yet another modified needle holder is shown in FIGS. 20 and 21 at 3018 and includes a first needle holding member 3112 in the form of an outer tubular sleeve 3126 with a lateral cut-out or window 3226 having a grasping surface 3120 formed on a proximal-facing surface or face of the window and a second needle holding member 3114 in the form of an inner tubular sleeve 3116 fitted telescopically within the outer tubular sleeve and having a grasping surface 3122 formed along a peripheral edge of the inner member to operate cooperatively with the grasping surface at the distal end of the outer member to hold a suture needle or other objects within the window. An auxiliary operating channel, shown by broken lines in FIG. 21 at 3118, may optionally be formed through the inner and outer members of the needle holder to permit access to the operative site via the channel from outside the body. If an auxilliary operating channel is not needed or desired, the second needle holding member 3114 can be solid instead of tubular, thus presenting a wider grasping surface if desired.

The window 3226 in the outer tubular sleeve 3126 of the modified needle holder 3018 can be oriented to face any suitable direction relative to the central longitudinal axis of the shaft 16 dependent upon the shape of the suture needle and procedural use. For example, the end effector window can be orientated to face inwardly, toward the central longitudinal axis, or outwardly, away from the central longitudinal axis, both of which orientations are shown in U.S. patent application Ser. No. 08/847,182, filed May 1, 1997, the disclosure of which is incorporated herein by reference.

FIG. 22 shows still another modification of a needle holder for use with the suturing instrument according to the present invention wherein the modified needle holder 4018 includes a first needle holding member 4112 in the form of a hook and a second needle holding member 4114 in the form of a keeper movable relative to the hook to capture and release a suture needle placed within the hook. The needle holding members are preferably formed of flat strips of a medically acceptable material, such as stainless steel, configured to lay flat against one and other to permit relative sliding movement of the needle holding members. The first needle holding member 4112 includes an elongate portion or leg 4228 extending distally from within the instrument housing to a bend 4230 where the first needle holding member folds inwardly upon itself to form a short leg 4232 parallel to the elongate portion or leg of the needle holding member thereby defining a hook with a proximal-facing mouth 4233 having a gap width suitable for receiving the shaft or body of a suture needle. The second needle holding member 4114 is slidingly disposed along the first needle holding member 4112 and includes a distal end 4234 configured to fit within the mouth of the hook as a keeper, the distal end of the second needle holding member being shown with an optional scalloped edge having one or more curved recesses. The first or second needle holding member may also be formed with a cutting member such as a blade or a notch of generally V-shaped configuration defined along an edge of the needle holding member and having one or more sharp edges to cut lengths of suture material received therein under pressure as shown, for example, by broken lines at 4236 in FIG. 22. The first needle holding member is also shown with optional slots or openings 4238a and 4238b formed on opposite sides of the hook to permit straight or slightly curved suture needles to be placed perpendicularly through short and long legs of the hook so as to be oriented radially relative to the longitudinal axis of the shaft. The slotted openings extend transversely, relative to a longitudinal axis of the needle holder, from respective open ends disposed along a lateral or longitudinal edge of the first needle holding member to generally centrally located terminal tends of rounded or semi-circular configuration with a size to receive the body or shank of a suture needle extending transversely through legs of the hook. As mentioned above, the scalloped edge at the distal end of the second needle holding member or keeper 4114 is configured with laterally spaced recesses, one of which is preferably aligned with a terminal portion or end of the slotted openings to cradle the needle positioned within the openings in a manner to secure the needle during linear suturing procedures wherein the suture needle is passed back and forth between the needle holders via lateral movement, for example as described in patent application Ser. No. 08/758,648, filed Nov. 27, 1996, the disclosure of which is incorporated herein by reference.

The modified needle holder 4018 shown in FIG. 22 can be positioned within the shaft 16 of the suturing instrument such that the mouth 4233 of the hook formed at the distal end of the needle holding member 4112 opens inwardly or outwardly relative to the central longitudinal axis 24 as shown, for example, in U.S. patent application Ser. No. 08/847,182, filed May 1, 1997, the disclosure of which is incorporated herein by reference.

Still another modification of a needle holder for use with the suturing instrument according to the present invention, as shown in FIGS. 23 and 24, includes a pair of needle holding members 5112 and 5114 in the form of jaws extending distally from a pair of crossed arms 5240a and 5240b connected by a pivot 5242 located medially along the lengths of the arms. A pair of elongate linkages 5244a and 5244b extend inwardly from pivots 5246a and 5246b at respective proximal ends of the arms to a pivot 5248 connecting the linkages with an elongate rod 5250. Linkages 5244*a* and 5244*b* are disposed on opposite sides of the rod, with pivot 5248 extending through the linkages and the rod and with tabs or ears 5252 extending laterally outward from the rod in opposite directions to overhang the linkages as stops preventing the linkages from spreading outwardly beyond a predetermined position. Jaws 5112 and 5114 are moved relative to one another by moving the outer tubular member and rod relative to one another. The jaws are normally biased apart, for example by a torsion spring coiled around a pivot and connected between the jaws, and are closed by moving the outer tubular member distally relative to the jaws, for example by advancing the outer tubular member distally and/or pulling the rod in the proximal direction. In a preferred embodiment, the outer tubular member is biased distally relative to the jaws so that the jaws are normally in a closed position.

From the above, it will be appreciated that the suturing instrument according to the present invention permits suturing of anatomical tissue during endoscopic procedures without the need of having to use multiple needle holding instruments inserted through multiple puncture sites by inserting an elongate shaft carrying a rotatably movable needle holder through a single puncture site. Preferably, the needle holder includes a distal portion movable between an undeployed, contracted or parked position spaced laterally inward of a peripheral edge of the elongate shaft to facilitate insertion through a portal sleeve and a deployed, expanded or working position where at least part of the distal portion is spaced laterally outward of the peripheral edge of the elongate shaft to permit use of suture needles having radii of curvature equal to or larger than a radial or lateral dimension of the elongate shaft and to permit suturing of thicker tissue by increasing the working span or range of travel of the needle holder. The elongate shaft is mounted by a handle with controls for moving the needle holder axially and in a rotary manner. The needle holder includes needle holding members selectively operable to grasp and release a suture needle so that, when the needle holding members are operated to grasp the suture needle, the needle holder can be moved in a direction to drive the suture needle through anatomical tissue, and when the needle holding members are released, the needle holder can be accurately repositioned to pick-up the other end of the suture needle so that it can be pulled through the tissue. Movement of the needle holder can be accomplished by rotating the needle holder relative to the elongate shaft or by rotating the needle holder with the elongate shaft as a unit.

The needle holder of the suturing instrument can be configured to hold needles of any size or shape including, but not limited to, needles with straight or curved bodies or shanks. While the needle holder is shown disposed within a cylindrical channel formed through the elongate shaft, it will be appreciated that the needle holder can be disposed within an arcuate channel, if desired, so that the needle holder can also be moved arcuately within the shaft about the center of curvature of the curved channel. A distal portion of the needle holder preferably extends laterally outward at an angle from the longitudinal axis of the elongate shaft to carry the needle holding members so that, when the needle holders are rotated about the longitudinal axis, the needle holding members are made to move arcuately along an arcuate path. Any type of needle holder can be modified for use with the suturing instrument according to the present invention by configuring a distal portion of the needle holder to be normally bent outwardly at an angle relative to the proximal portion, including, but not limited to, any of the needle holders described in U.S. patent applications Ser. No. 081758,648, filed Nov. 27, 1996, and Ser. Nos. 08/847,182, 08/847,254, 08/847,253, 08/847,189, and 08/847,252, filed May 1, 1997, the disclosures of which are incorporated herein by reference. For example, any of the needle holders can include a transverse connecting member extending perpendicularly outward from a proximal portion of the needle holder to needle holding members laterally offset from the proximal portion.

One or more lengths of suture material can be attached to each suture needle at any desirable location along the body of tip of the needle including, but not limited to, the proximal end of the needle, intermediate or medial portions of the needle body, or locations adjacent the tip of the needle. It will also be appreciated that the suturing instrument according to the present invention can be used with suture needles having sharp or blunt tissue penetrating tips, and needles having tissue penetrating tips at opposite axial ends of a needle body.

The needle holding members of the needle holder shown and described herein are exemplary of the types of needle holding members that can be used according to the present invention. Accordingly, the needle holding members can have any suitable configuration for individually or cooperatively grasping needles to suture anatomical tissue including, but not limited to, jaw-like configurations wherein the needle holding members pivot, slide or otherwise move relative to one another to capture and release a needle. The needle holding members can be of straight, curved or angled configuration and can be provided with ribs, grooves, slots and/or holes along grasping surfaces to assure a positive grip. The needle holding members can also carry cutting members, such as slots with sharp edges or protruding blades, and can have opposed arcuate or concave portions for clamping tubular objects, such as organs, without compressing the objects, as well as portions configured to take a tissue sample for biopsy. When the needle holding members are carried at the distal end of one or more elongate components, for example a rod telescopically fitted within a tube, either component can include a distal portion of predetermined shape which, in an unrestrained condition, bends laterally outward at an angle relative to the longitudinal axis of the proximal portion of the needle holder component. Furthermore, components of a needle holder can be keyed or coupled to move together so that, for example, if one of the components is rotated the other component will be rotated as well.

The needle holder of the present invention can also be used as an end effector to perform lysis of adhesion, dissection, pickup and cutting, pickup and clipping, pickup and suturing with a suture needle, unipolar and bipolar electrosurgery, and numerous other procedures. Although the suturing instrument is shown and described herein as having a single needle holder, it will be appreciated that two or more needle holders can be used dependent upon the procedure to be performed and the preference of the user. When more than one needle holder is used, the additional needle holders can be straight or they can bend at a distal end like the needle holder described above. Also, the needle holder can be positioned at any location across the width or lateral extent of the shaft.

Although the elongate shaft is shown as being composed of optical fibers disposed within a tubular sleeve, it will be appreciated that the elongate shaft can be formed without a separate sleeve, for example by embedding or molding the optical fibers within a medically acceptable polymer matrix or by adhesively connecting the fibers together. The elongate shaft can also be formed without optical fibers extending therethrough, in which case a light source may be inserted through one of the channels defined through the shaft or through a separate puncture to illuminate the operative site. The shaft can be rigid or flexible and can be made of any suitable medically acceptable material, such as plastic or stainless steel. The cross-sectional configuration of the outer surface of the shaft is preferably circular as shown but can be elliptical, polygonal or have any other configuration suitable for a particular purpose. The distal end or face of the shaft can be flat as shown, convex or concave; and, when flat, the distal face can be oriented at any angle relative to the longitudinal axis of the shaft. While four channels are shown in addition to the needle holder channel, any number of channels can be formed through the elongate shaft, for example by thin wall, tubular sleeves extending longitudinally through the shaft or by voids or spaces defined between the optical fibers as shown. The channels can be parallel to one another or oriented at angles, can be straight or curved, and can be of constant or varying lateral dimension along their length. Furthermore, the channels can be located anywhere within the elongate shaft and can be of the same or different design dependent upon procedural use and space constraints.

The operating channels can have any configuration in transverse cross-section including, but not limited to, elliptical, polygonal and irregular or asymmetrical cross-sectional configurations. Also, all or part of the inner surface of a channel can be electrically insulated to permit passage of electrosurgical instruments therethrough. The valves and couplings shown at the proximal end of each channel are merely exemplary of the types of conventional valves and conventional couplings that can be used. Operating channels may also be defined along the length of the needle holder of the instrument, if desired. It will also be appreciated that storage spaces or recesses can be defined in the elongate shaft to hold suture needles, lengths of suture material, or other devices.

It will be appreciated that other handle configurations can be used including, but not limited to, configurations wherein the handle includes pivoted legs with finger loops, one fixed and one pivoted leg with finger loops, a pistol grip with one or more movable triggers, and/or resilient U-shaped members. Moreover, the handle can have adjustable handle members of variable orientation as shown or handle members which are fixed in a specific orientation relative to the housing. If desired, the housing and at least a portion of the handle can be formed as an integral one-piece unit.

The mechanisms shown for controlling operation of the needle holding members of the needle holder and movement of the needle holder relative to the shaft are merely exemplary of the types of mechanisms that can be used to perform these functions. For example, in the case of slidable needle holding members, mechanisms including, but not limited to, controls in the form of push-buttons with wedge-shaped members for engaging flanges carried by each member, resilient U-shaped members with arms connected to each member, and triggers connected to the members via linkages or gears can be used to cause the needle holding members to move relative to one another. In the case of pivoted needle holding members or jaws, mechanisms such as tubular members movable relative to the jaws or linkages connecting one or both of the jaws with a trigger or the like at a proximal end of the instrument can be used to cause the needle holding members or jaws to move relative to one another. The needle holding members can be biased to a particular position, condition or state, such as an open state for receiving a suture needle or a closed state for grasping a suture needle, and can be provided with locking features to permit the user to maintain the members in a desired position.

Moving the needle holder relative to the shaft can be accomplished in any suitable manner, for example by connecting a knob at the proximal end of each needle holding instrument and sliding the knobs along slots formed in the handle housing or by mounting the needle holding instruments on geared components and moving the gears with a trigger or some other device. The particular length and curvature of the suture needles shown and described herein as well as any angular displacements of the needle holder and catcher shown and described herein are merely exemplary, and it will be appreciated that other needle lengths and angular displacements can be used. It will also be appreciated that the directions and angles of rotation of the needle holder described and shown herein are for purposes of illustration only and can be reversed and/or altered in magnitude dependent upon procedural use and the preferences of the user.

While the needle holder has been described herein as having a normally bent configuration which can be straightened by retracting the needle holder in a proximal direction relative to a tubular member so as to elastically deform the needle holders, it will be appreciated that the needle holder of the present invention can be moved between contracted and expanded positions using any suitable method including, but not limited to, methods utilizing linkages, gears, cables, movable stiffeners or inserts, shape memory materials, actuators or motors. Dependent upon the angular deflection and length of the bent or angled distal portions of the needle holders, the distal portions may be movable between deployed and parked positions merely by rotation about their respective axes. Also, distal portions of the needle holders need not be straight as shown but can be curved or multiply angled, if desired.

The components of the suturing instrument of the present invention can be made of any suitable, medical grade materials to permit sterilization for reuse or disposal for single patient use. The components can be made of multiple parts of various configurations and materials to reduce cost. The housing and/or handle can have various valves, stop cocks and seals therein to control the flow of fluid and medical devices through the suturing instrument.

The features of the various embodiments described above can be combined in any manner desired dependent upon the operational requirements of the procedure to be performed and the complexity of the suturing instrument. It will also be appreciated that the suturing instrument of the present invention can be used to apply single or multiple stitches in open or endoscopic procedures.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. An instrument for suturing anatomical tissue with a suture needle, said suturing instrument comprising
   an elongate shaft having a proximal end and a distal end with a peripheral edge;
   a handle coupled to said proximal end of said elongate shaft; and
   an arm protruding from said distal end of said elongate shaft and having a needle holding portion at a distal end operable to grasp and release a suture needle, said arm extending laterally outward at an angle from a longitudinal axis within said elongate shaft to a position where at least a portion of said needle holding portion is spaced laterally outward of said peripheral edge of said elongate shaft, said arm further being rotatable about said longitudinal axis to cause said needle holding portion to move along an arcuate path having a center of curvature coaxial with said longitudinal axis.

2. A suturing instrument as recited in claim 1 wherein said needle holding portion is movable between an undeployed position where said needle holding portion is spaced laterally inward of said peripheral edge of said elongate shaft and a deployed position where at least a portion of said needle holding portion is disposed laterally outward of said peripheral edge.

3. A suturing instrument as recited in claim 2 wherein said arm is disposed on an elongate proximal member extending at least partly through said shaft in coaxial alignment with said longitudinal axis.

4. A suturing instrument as recited in claim 3 wherein said arm is longitudinally movable relative to said elongate shaft between an axially extended position where said arm bends outwardly in a lateral direction relative to said longitudinal axis and an axially retracted position where said arm is drawn inwardly toward said longitudinal axis.

5. A suturing instrument as recited in claim 4 wherein said needle holding portion is proximally spaced from said distal end of said shaft in said retracted position.

6. A suturing instrument as recited in claim 1 wherein a radius of curvature of said arcuate path is substantially commensurate with a radius of curvature of said suture needle.

7. A suturing instrument as recited in claim 1 and further comprising an operating channel defined through said elongate shaft to provide access to the operative site from outside the body.

8. A suturing instrument as recited in claim 1 and further comprising a plurality of operating channels defined through said elongate shaft in laterally spaced relation to provide access to the operative site from outside the body.

9. A suturing instrument as recited in claim 7 further comprising a housing coupled to said proximal end of said elongate shaft and wherein said operating channel extends through said housing to define a longitudinal channel along the length of said instrument, and further comprising a coupling at a proximal end of said channel.

10. A suturing instrument as recited in claim 7 further comprising a housing coupled to said proximal end of said elongate shaft and wherein said operating channel extends through said housing to define a longitudinal channel along the length of said instrument, and further comprising a valve disposed along said longitudinal channel to control passage of fluids and instruments therethrough.

11. A suturing instrument as recited in claim 1 wherein an operating channel is defined through said arm to provide access to the operative site from outside the body.

12. A suturing instrument as recited in claim 11 wherein said arm is disposed on an elongate proximal member extending through said elongate shaft and wherein said operating channel terminates distally at an opening adjacent the junction between said proximal member and said arm.

13. A suturing instrument as recited in claim 1 wherein said needle holding portion includes a pair of cooperating needle holding members.

14. A suturing instrument as recited in claim 13 wherein at least one of said needle holding members carries a cutting member.

15. A suturing instrument as recited in claim 13 wherein said needle holding members include a pair of pivotally opposed jaws.

16. A suturing instrument as recited in claim 15 wherein both of said jaws move relative to one another.

17. A suturing instrument as recited in claim 15 wherein a first of said jaws is fixed and a second of said jaws is movable relative to said first jaw.

18. A suturing instrument as recited in claim 15 wherein said arm includes a pair of telescoping inner and outer members axially movable relative to one another, said jaws being mounted at the distal end of said inner telescoping member and being biased apart to an open position such that relative axial movement of the inner and outer telescoping members results in opening and closing of said jaws.

19. A suturing instrument as recited in claim 13 wherein said needle holding portion includes a first needle holding member having a distal end in the form of a hook and a second needle holding member having a distal end movable relative to said hook to grasp and release suture needles disposed within said hook.

20. A suturing instrument as recited in claim 13 wherein said needle holding portion includes a first needle holding member in the form of a tube with a lateral window formed therethrough and a second needle holding member having a distal end movable axially within said tube to grasp and release suture needles disposed within said window.

21. A method of suturing anatomical tissue using a length of suture material attached to a suture needle, said method comprising the steps of grasping the suture needle with a needle holding portion of an arm, the arm protruding distally from the distal end of an elongate shaft and extending laterally outward at an angle from a first longitudinal axis within the elongate shaft the needle holding portion being disposed at least partly outside a peripheral edge of the elongate shaft;

positioning a tip of the suture needle adjacent the anatomical tissue;

driving the suture needle through the anatomical tissue along an arcuate path by rotating the arm in a first direction;

releasing the suture needle from the needle holding portion;

repositioning the needle holding portion to receive the tip of the suture needle by rotating the arm in a second direction opposite the first direction;

regrasping the suture needle with the needle holding portion; and pulling the suture needle through the anatomical tissue by rotating the arm in the first direction.

22. A method of suturing anatomical tissue as recited in claim 21 and further comprising, prior to said step of driving the suture needle, the step of causing the needle holding portion to move laterally outward from an undeployed position spaced inwardly of the peripheral edge of the elongate shaft to a deployed position spaced outwardly of the peripheral edge of the elongate shaft.

23. A method of suturing anatomical tissue as recited in claim 21 and further comprising, prior to said step of driving the suture needle, the step of causing the arm to move distally relative to the elongate shaft from an axially retracted position within the elongate shaft to an axially extended position protruding from the distal end of the elongate shaft.

24. A method of suturing anatomical tissue as recited in claim 21 wherein said step of driving the suture needle includes the step of rotating the arm in the first direction about the longitudinal axis to cause the needle holding portion to move arcuately.

25. A method of suturing anatomical tissue as recited in claim 21 wherein said step of driving the suture needle includes the step of rotating the shaft of the instrument in the first direction to cause the needle holding portion to move arcuately.

26. A method of suturing anatomical tissue as recited in claim 21 wherein said step of pulling the suture needle includes the step of rotating the arm in the first direction about the longitudinal axis to cause the needle holding portion to move arcuately.

27. A method of suturing anatomical tissue as recited in claim 21 wherein said step of pulling the suture needle includes the step of rotating the shaft of the instrument in the first direction to cause the needle holding portion to move arcuately.

28. A method of suturing anatomical tissue using a length of suture material attached to a suture needle, said method comprising the steps of:

grasping the suture needle with a needle holding portion of an arm, the arm protruding distally from the distal end of an elongate shaft and extending laterally outward at an angle from a first longitudinal axis within the elongate shaft, the needle holding portion being disposed at least partly outside a peripheral edge of the elongate shaft;

positioning a tip of the suture needle adjacent the anatomical tissue;

driving the suture needle through the anatomical tissue by moving the needle holding portion in a first direction toward the longitudinal axis within the elongate shaft;

releasing the suture needle from the needle holding portion;

repositioning the needle holding portion to receive the tip of the suture needle;

regrasping the suture needle with the needle holding portion; and pulling the suture needle through the anatomical tissue by moving the needle holding portion in a second direction opposite the first direction.

* * * * *